(12) United States Patent
Tadigadapa et al.

(10) Patent No.: US 10,578,594 B2
(45) Date of Patent: Mar. 3, 2020

(54) BIOCHEMICAL SENSING USING MICROBUBBLES ON A CHIP USING WHISPERING GALLERY MODE RESONANCE

(71) Applicant: The Penn State Research Foundation, University Park, PA (US)

(72) Inventors: Srinivas Tadigadapa, State College, PA (US); Eugene Freeman, St Louis Park, MN (US); Chenchen Zhang, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 153 days.

(21) Appl. No.: 15/855,360

(22) Filed: Dec. 27, 2017

(65) Prior Publication Data
US 2018/0180580 A1    Jun. 28, 2018

Related U.S. Application Data

(60) Provisional application No. 62/439,310, filed on Dec. 27, 2016.

(51) Int. Cl.
*G01N 30/74* (2006.01)
*B01D 53/02* (2006.01)
(Continued)

(52) U.S. Cl.
CPC ........... *G01N 30/74* (2013.01); *B01D 53/025* (2013.01); *B01L 3/502715* (2013.01);
(Continued)

(58) Field of Classification Search
CPC ........ G01N 30/74; G01N 30/62; G01N 30/02; G01N 30/00; B01D 53/025; B01D 53/02;
(Continued)

(56) References Cited

U.S. PATENT DOCUMENTS 7,693,369 B2 * 4/2010 Fan .................... G01N 21/7746
                                                                385/2
8,107,081 B2   1/2012 Armani et al.
(Continued)

FOREIGN PATENT DOCUMENTS

EP    2916125 A1    9/2015
EP    2927689 A1    10/2015
(Continued)

OTHER PUBLICATIONS

Sun, Yuze, Optofluidic Ring Resonator: A Versatile Microfluidic Platform for Chemical Vapor Detection and Intra-Cavity Biomolecular Analysis, Dissertation, The University of Michigan, 2011, pp. 1-143. (Year: 2011).*

(Continued)

*Primary Examiner* — Christine T Mui
(74) *Attorney, Agent, or Firm* — Dana M. Gordon; Foley Hoag LLP

(57) ABSTRACT

A sensing and analysis system on a chip for sensing and analyzing chemical or biological analytes includes a chromatography column having an inlet and an outlet formed on the chip for temporal separation of components of analytes and at least one whispering gallery mode (WGM) optical resonator for sensing of the components. The chromatography column is formed on a first wafer layer. Each WGM optical resonator includes a hollow sealed enclosure formed at or over the inlet or the outlet of or elsewhere along the chromatography column such that a gas flowing through the chromatography column fills the hollow sealed enclosure. Each WGM optical resonator further includes an optical waveguide aligned with the sealed hollow enclosure for evanescent wave light coupling.

18 Claims, 16 Drawing Sheets

(51) Int. Cl.
| | |
|---|---|
| *B01L 3/00* | (2006.01) |
| *G01N 33/487* | (2006.01) |
| *G01N 30/88* | (2006.01) |
| *G01N 25/48* | (2006.01) |
| *G01N 30/60* | (2006.01) |
| *G02B 6/293* | (2006.01) |
| *G01K 17/00* | (2006.01) |

(52) U.S. Cl.
CPC .... *B01L 3/502753* (2013.01); *G01N 25/4813* (2013.01); *G01N 30/6095* (2013.01); *G01N 30/88* (2013.01); *G01N 33/487* (2013.01); *B01L 2200/10* (2013.01); *B01L 2300/0654* (2013.01); *B01L 2300/0816* (2013.01); *B01L 2300/0848* (2013.01); *G01K 17/006* (2013.01); *G01N 2030/8813* (2013.01); *G02B 6/29341* (2013.01)

(58) Field of Classification Search
CPC ... B01D 53/00; B01L 3/52715; B01L 3/5027; B01L 3/502; B01L 3/50
USPC .......................................... 422/502, 500, 50
See application file for complete search history.

(56) References Cited

U.S. PATENT DOCUMENTS

| | | | |
|---|---|---|---|
| 8,151,600 | B2 | 4/2012 | Eklund et al. |
| 9,316,623 | B2 | 4/2016 | Seo et al. |
| 2010/0142887 | A1 | 6/2010 | Digonnet et al. |
| 2012/0268731 | A1 | 10/2012 | Zhu et al. |
| 2013/0157283 | A1 | 6/2013 | Yung et al. |
| 2015/0023633 | A1 | 1/2015 | Digonnet et al. |
| 2016/0167052 | A1 | 6/2016 | Carmon et al. |
| 2016/0266110 | A1 | 9/2016 | Ozdemir et al. |
| 2018/0180580 | A1 | 6/2018 | Tadigadapa et al. |

FOREIGN PATENT DOCUMENTS

| | | | |
|---|---|---|---|
| WO | 2011133670 | A2 | 10/2011 |
| WO | WO-2015/126517 | A2 | 8/2015 |

OTHER PUBLICATIONS

Gaddes D. et al. Improved micromachined column design and fluidic interconnects for programmed high-temperature gas chromatography separations; Journal of Chromatography A, 1349 (2014) 96-104; http://dx.doi.org/10.1016/j.chroma.2014.04.087.
Gaddes D.E. et al. Remote calorimetric detection of urea via flow injection analysis; The Royal Society of Chemistry 2015, Analyst, 2015, 140, 8033-8040.
Scholten K. W. et al. Nanoparticle-Coated Micro-Optofluidic Ring Resonator as a Detector for Microscale Gas Chromatographic Vapor Analysis; Royal Society of Chemistry, Issue 20, 2015.
Sumetsky M. et al. Optical microbubble resonator; Optical Society of America, 2010, Optics Letters, vol. 35, No. 7, Apr. 1, 2010, pp. 898-900.
Zhang C. et al. On-Chip Glass Microspherical Shell Whispering Gallery Mode Resonators; Scientific Reports 7, Article No. 14965 (2017), DOI:10.1038/s41598-017-14049-w.
Zhang C. et al. Whispering Gallery Mode Based On-Chip Glass Microbubble Resonator for Thermal Sensing; 2017 19th International Conference on Solid-State Sensors, Actuators and Microsystems (Transducers), Jun. 18-22, 2017, Kaohsiung, Taiwan.
Agah et al., "High-performance temperature-programmed microfabricated gas chromatography columns," Journal of Microelectromechanical Systems, 14(5):1039-1050 (2005).
Almeida et al., "Nano-taper for compact mode conversion," Optics Letters, 28(15):1302-1304 (2003).

Carey et al., "Selection of Adsorbates for Chemical Sensor Arrays by Pattern-Recognition," Analytical Chemistry, 58(1):149-153 (1986).
Cho et al., "Fused-Silica Micro Birdbath Resonator Gyroscope," Journal of Microelectromechanical Systems, 23(1):66-77 (2014).
Cross et al., "Refractometric discrimination of void-space filling and swelling during vapour sorption in polymer films," Analyst, 125(12):2173-2175 (2000).
Danielsson, "Calorimetric Biosensors," J. Biotechnology, 15(3):187-200 (1990).
Eklund et al., "Glass blowing on a wafer level," Journal of Microelectromechanical Systems, 16(2):232-239 (2007).
Gaddes et al., "Calorimetric Biosensing System for Quantification of Urinary Creatinine," ACS Sensors, 2(6):796-802 (2017).
Grate et al., "Solubility interactions and the design of chemically selective sorbent coatings for chemical sensors and arrays," Sensors and Actuators B: Chemical, 3(2):85-111 (1990).
Harsanyi, "Polymer films in sensor applications : technology, materials, devices and their characteristics," Lancaster, Pa.: Technomic Pub. Co. xxvi, 435 (1995).
Hatipoglu et al., "A highly aromatic and sulfonated ionomer for high elastic modulus ionic polymer membrane micro-actuators," Smart Materials and Structures, 21(5):055015 (2012).
Heilig et al., "Gas identification by modulating temperatures of SnO2-based thick film sensors," Sensors and Actuators B-Chemical, 43(1-3):45-51 (1997).
Hierlemann et al., "Polymer-Based Sensor Arrays and Multicomponent Analysis for the Detection of Hazardous Organic Vapors in the Environment," Sensors and Actuators B-Chemical, 26(1-3):126-134 (1995).
Jin et al., "Enhancing the sensitivity of ionic liquid sensors for methane detection with polyaniline template," Sensors and Actuators B: Chemical, 133(2):526-532 (2008).
Jin et al., "Ionic Liquid High-Temperature Gas Sensor Array," Analytical Chemistry, 78(19):6980-6989 (2006).
Kao et al., "Study of Adsorption of Globular Proteins on Hydrophobic Surfaces," IEEE Sensors Journal, 11(11):2723-2731 (2011).
Kao et al., "Volumetric interpretation of protein adsorption: Interfacial packing of protein adsorbed to hydrophobic surfaces from surface-saturating solution concentrations," Biomaterials, 32(4):969-978 (2011).
Ksendzov et al, "Integrated optics ring-resonator chemical sensor with polymer transduction layer," Electronics Letters, 40(1):63-65 (2004).
Lambertus et al., "Design, Fabrication, and Evaluation of Microfabricated Columns for Gas Chromatography," Analytical Chemistry, 76(9):2629-2637 (2004).
Lee et al., "High-sensitivity microfluidic calorimeters for biological and chemical applications," Proceedings of the National Academy of Sciences, 106(36):15225-15230 (2009).
Lerchner et al., "Calorimetric detection of volatile organic compounds," Sensors and Actuators B, 70:57-66 (2000).
Lin et al., "A selective room temperature formaldehyde gas sensor using TiO(2) nanotube arrays," Sensors and Actuators B-Chemical, 156(2): 505-509 (2011).
Ma et al., "Temperature sensitivity of silica micro-resonators," Journal of Physics D: Applied Physics, 41(24):245111 (2008).
Michels et al., "Cavity optical transducer platform with integrated actuation for multiple sensing applications," Solid State Sensors, Actuators, and Microsystems Workshop, Transducers Research Foundation: Hilton Head Island, SC. p. 4 (2016).
Min et al., "Designing chemically selective microsensor arrays using ionic liquid doped ionomers," IEEE Sensors (2013).
Min, "Study of Interfacial Phenomena for Bio/Chemical Sensing Applications," Dissertation in Pennsylvania State University Electrical Engineering, 1-173 (2014).
Moerman et al., "A review on fabrication technologies for the monolithic integration of tapers with III-V semiconductor devices," IEEE Journal of Selected Topics in Quantum Electronics, 3(6):1308-1320 (1997).
Nakata et al., "Gas sensing based on a nonlinear response: Discrimination between hydrocarbons and quantification of individual components in a gas mixture," Analytical Chemistry, 68(13): p. 2067-2072 (1996).

(56) References Cited

OTHER PUBLICATIONS

Pisani et al., "Application of micromachined Y-cut quartz bulk acoustic wave resonator for infrared sensing," Journal of Microelectromechanical Systems, 20(1):288-296 (2011).
Podgorsek et al., "Selective optical detection of aromatic vapors," Applied Optics, 41(4):601-608 (2002).
Potyrailo et al., "Boosting Sensitivity of Organic Vapor Detection with Silicone Block Polyimide Polymers," Analytical Chemistry, 76(23):7023-7027 (2004).
Reidy et al., "Temperature-Programmed GC Using Silicon Microfabricated Columns with Integrated Heaters and Temperature Sensors," Analytical Chemistry, 79(7):2911-2917 (2007).
Ren et al., "Monitoring biochemical reactions using Y-cut quartz thermal sensors," Analyst, 136:2904-2911 (2011).
Rose-Pehrsson et al., "Detection of Hazardous Vapors Including Mixtures Using Pattern-Recognition Analysis of Responses from Surface Acoustic-Wave Devices," Analytical Chemistry, 60(24):2801-2811 (1988).
Shopova et al., "On-Column Micro Gas Chromatography Detection with Capillary-Based Optical Ring Resonators," Analytical Chemistry, 80(6):2232-2238 (2008).
Sun et al., "Analysis of ring resonators for chemical vapor sensor development," Optics Express, 16(14):10254-10268 (2008).
Terry et al., "A gas chromatographic air analyzer fabricated on a silicon wafer," IEEE Transactions on Electron Devices, 26(12):1880-1886 (1979).
Tigelaar et al., "Synthesis and Properties of Novel Proton-Conducting Aromatic Poly(ether sulfone)s That Contain Triazine Groups," Macromolecules, 42(6):1888-1896 (2009).
Tomchenko et al., "Semiconducting metal oxide sensor array for the selective detection of combustion gases," Sensors and Actuators B-Chemical, 93(1-3):126-134 (2003).
van Herwaarden et al., "Integrated thermopile sensors," Sensors and Actuators A: Physical, 22(1-3):621-630 (1989).
van Herwaarden et al., "Liquid and gas micro-calorimeters for (bio)chemical measurements," Sensors and Actuators A: Physical, 43(1-3):24-30 (1994).
Vig et al., "Uncooled IR imaging array based on quartz microresonators," Journal of Microelectromechanical Systems, 5(2):131-137 (1996).
Xie et al., "Fabrication and formaldehyde gas-sensing property of ZnO-MnO2 coplanar gas sensor arrays," Sensors and Actuators B-Chemical, 145(1):457-463 (2010).
Zhang et al, "High-Speed Ultrasmooth Etching of Fused Silica Substrates in SF6, NF3, and H2O-Based Inductively Coupled Plasma Process," Journal of Microelectromechanical Systems, 24(4):922-930 (2015).
Zhang et al., "Calorimetric biosensors with integrated microfluidic channels," Biosensors and Bioelectronics, 19(12):1733-1743 (2004).

* cited by examiner

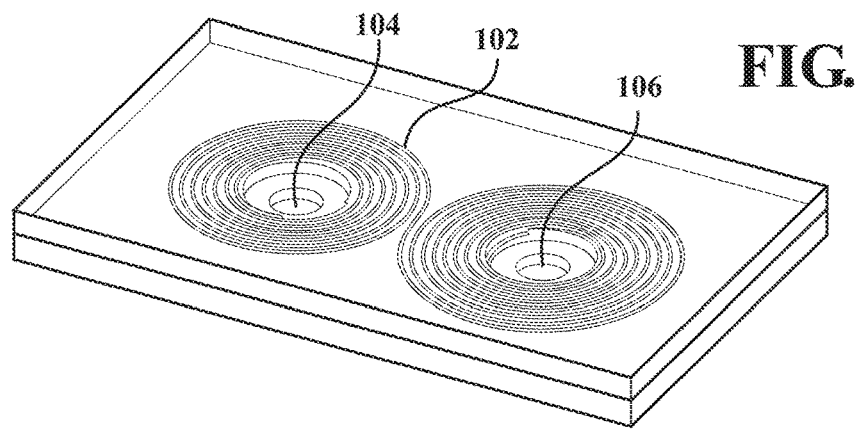
FIG. 1A
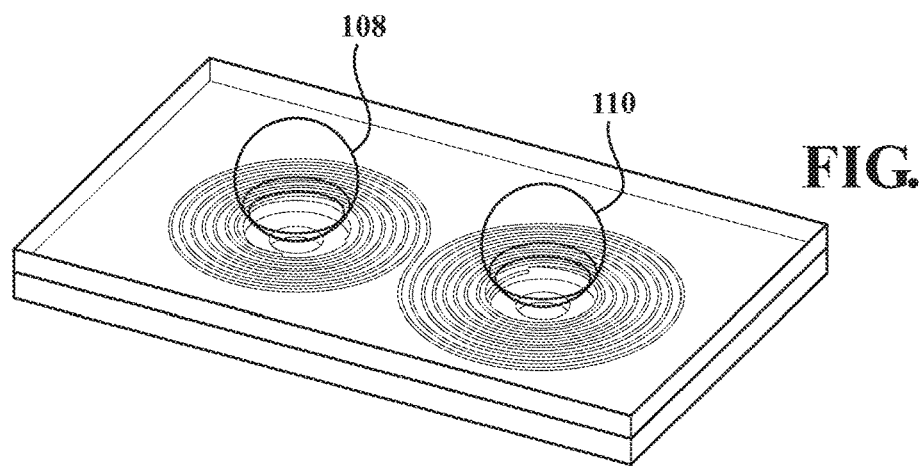
FIG. 1B
FIG. 1C
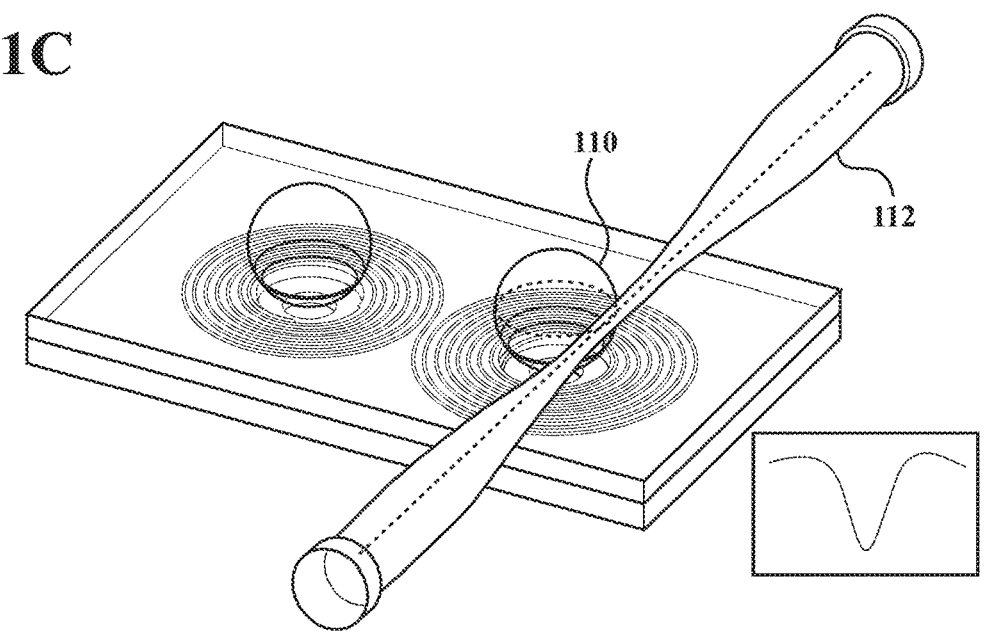

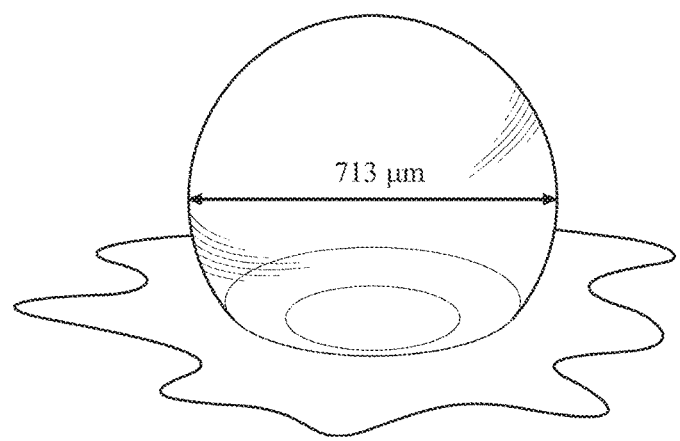
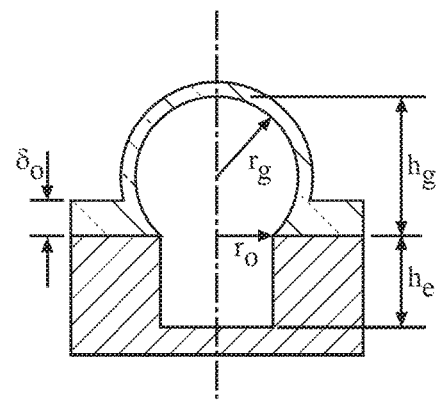
FIG. 5A
FIG. 5B
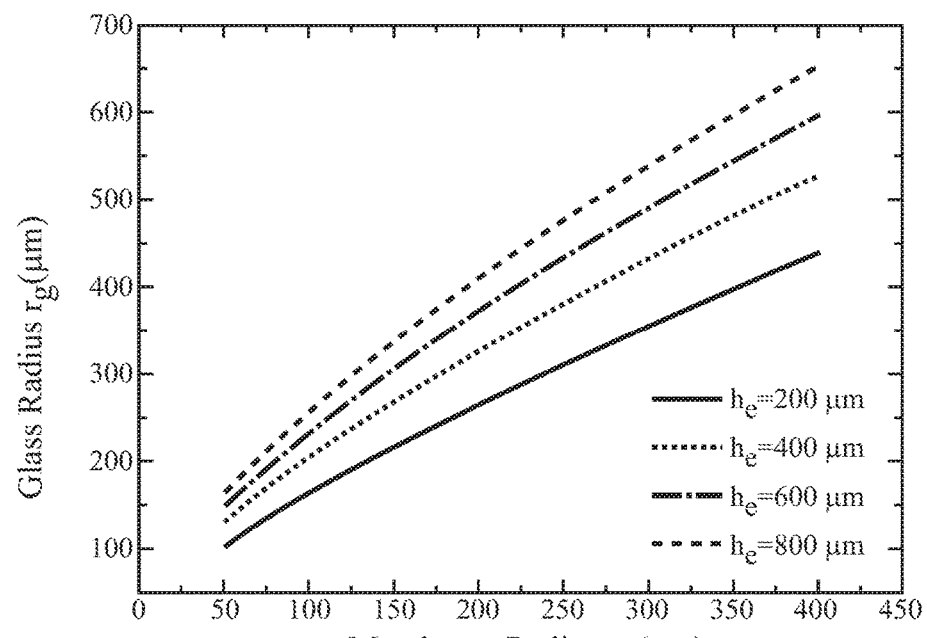
FIG. 5C

BIOCHEMICAL SENSING USING MICROBUBBLES ON A CHIP USING WHISPERING GALLERY MODE RESONANCE

REFERENCE TO RELATED APPLICATION

This application claims priority from U.S. Provisional Patent Application Ser. No. 62/439,310, filed Dec. 27, 2016, the entire content of which is incorporated herein by reference.

FIELD OF THE INVENTION

The present invention relates to a micro chemical and biochemical analysis system on a chip exploiting integration of microbubble-based whispering gallery mode sensors with on-chip chromatography columns, or calorimetric on-chip device, or other on-chip biochemical devices.

BACKGROUND OF THE INVENTION

Inexpensive and compact chemical analysis systems capable of gas discrimination and quantification are highly desirable especially in the context of rapidly developing mobile sensing and monitoring platforms. Similarly there is also a rapidly developing need for point of care devices for bioanalytical detection of markers of health and disease. Such systems can provide vital information for environmental monitoring, breath analysis, health monitoring, and safety & security systems. While significant progress has been made in recent years in the analysis of gas recognition using various types of transducers coated with a variety of receptor materials [1-10] achieving reliable recognition and their quantification continues to remain as a challenge. In this context, the gas discrimination outcomes achieved through exposure of a spatial array of selectively decorated pixels to an analyte mixture can be vastly improved through a simultaneous temporal separation of the gas mixture components through chromatography. Furthermore, ultrasensitive thermal sensors can be configured into biosensors for selective detection of various bioanalytes [11-16]. In spite of several advantages, thermal biosensors have not been able to achieve the same acceptance as other detection approaches largely due to either large volumes of the required samples or due to the performance degradation arising from the extremely fragile construction and cumbersome functionalization approaches suitable for chip scale calorimeters. This proposal aims to address these shortcomings and proposes a novel whispering gallery mode (WGM) resonator based solution for these challenges.

On-Chip Chromatography:

Chromatography offers a simple way to temporally separate the components in an analyte sample and therefore achieve component discrimination. One of the first analytical components developed using microfabrication techniques was the micro gas chromatograph (μGC) on chip [17]. Microfabricated columns of length equal to their commercial counter parts occupy significantly less space, are batch fabricated and thus can be produced very inexpensively [18]. As compared to conventional columns which require large power [19], the small thermal mass of the chip-sized, microfabricated columns allows for rapid heating and cooling at significantly less power [20, 21]. Finally, miniaturized analytical systems benefit from the favorable scaling laws such as increased surface area to volume ratio. However, integrating μGC columns with in-line high-sensitivity detectors for sensing the elution components proved to be very challenging and has compromised their overall performance.

SUMMARY OF THE INVENTION

The present invention provides a microbubble based whispering gallery mode (WGM) sensing solution for realizing a high-performance chip-scale Total Analysis System (TAS) through the integration of microbubble based WGM optical resonators with on-chip chemical or biochemical sensing or analysis device such as chromatography columns or biochemical reaction chambers on a chip. The Q-factor of the optical resonance according to the present invention may be up to above 100 million.

The microbubble in the chip-scale TAS can be the shape of a near spherical shell, a toroidal shell, a double walled shell, or a shell of any thickness and shape blown out using the planar glass blowing technique described herein.

The chromatography column may have a double Archimedean, square, rectangular, elliptical, triangular, or other concentric spiral geometry. The chromatography column may have an inlet and an outlet. Due to the spiral geometry, the chromatography column can be very long. In one example, the chromatography column is 1-10 m long. A channel of the chromatography column may a cross-section having a dimension ranging from 100 micron×100 micron to 500 micron×500 micron.

The microbubbles may have an inner surface and an outer surface. The microbubbles may be a hollow sealed enclosure formed at or over the inlet or the outlet of the chromatography column or elsewhere along the chromatography column. The inner surface of the microbubbles may be in connection with the chromatography column such that a gas flowing through the chromatography column fills the hollow sealed enclosure. In one version, a microbubble is only formed at or over the outlet of the chromatography column. In another version, a microbubble may be formed at or over both the inlet and outlet of the chromatography column.

In one example, the on-chip chromatography columns and the inner surface of the microbubbles may be functionalized with polydimethylsiloxane (PDMS) or other functional coatings based on room temperature ionic liquids (RTILs) in a polymeric matrix as the stationary phase. The refractive index of the coating may change with the presence of the analytes. The reaction of the analytes with the coating may also change the refractive index of the coating. The analytes can then be detected based on the change of the refractive index of the light.

According to an embodiment of the present invention, an optical waveguide may be aligned with the microbubble for evanescent wave light coupling. The optical waveguide may be tapered towards the microbubble for achieving optimal coupling of the evanescent wave into the microbubble.

According to an objective of the present invention, a chemical/biochemical reaction or process takes place within the microbubbles and on the inner surface of the microbubbles. The optical resonance is induced through the outer surface of the microbubbles. Due to the sealed enclosure and integrated structure of the microbubble with the chromatography column, there will be no loss of the analytes to the outside of the microbubbles.

The microbubbles may be formed with wafer scale glass blowing techniques demonstrated to create hemispherical and toroidal structures from glass and fused silica on a chip. [22, 23] Such glass structures on a chip can have very small thicknesses and a very smooth surface and can be exploited for realizing whispering gallery mode (WGM) optical resonators with exceptionally high Q-factors.

In some versions, the present invention explores the relationship between the polymer layer thickness and the Q-factor/finesse of the resonator in order to optimize the shell thickness and polymer layer to achieve highest optical resonator sensitivity. The glass microspherical shells can range in diameters from 50 μm to over 1 mm with wall thicknesses that can be controlled in the range of 50 nm to 100 s of μm. The smoothness of the bubble surfaces can range from sub-Angstrom range into nanometers due to the reflow process.

The fabrication process in the present invention allows for the monolithic integration of a microbubble structure based optical resonator and on-chip chromatography columns into a single device structure.

According to one embodiment, the device of the present invention may include a first wafer layer patterned and etched to form a chromatography column, a glass layer aligned and bonded to the first wafer layer, and a microbubble blown from the glass layer at the patterned and etched region.

In one version, the device of the present invention may include an inlet and outlet region etched on the first wafer layer with a microbubble blown at each region.

The chip-scale TAS of the present invention may also include a three wafer stack structure. In this version, a third wafer layer has the optical waveguides attached thereon and through holes etched therein so as to allow for the microbubbles to be able to pass therethrough. The third wafer layer may be aligned and bonded to the glass layer, such that a top surface of the third wafer layer is at an equatorial plane of the microbubble when the three wafer stack is bonded together and the optical waveguide is positioned to achieve optimal coupling of an evanescent wave into the microbubble.

According to another embodiment, the present invention provides a calorimetric biosensor where a microfluidic channel is integrated with the microbubble using an integrated on-chip microbubble structure as a sensitive thermometer and using immobilized enzymatic functionalization for selective detection of bioanalytes of interest.

A selective biocatalyst of interest such as any selective molecules, enzymes, or proteins, or cells or a mixture thereof is placed in the microfluidic channel. The heat generated or absorbed upon reaction of the bioanalyte of interest with the biocatalyst is directly coupled to the temperature-dependent microbubble based WGM resonator and is the principle of calorimetric microbubble WGM sensor.

In this embodiment, the first wafer layer may be molded to create fluidic channels and a reactor pit, the mold including an inlet chamber followed by an immobilization chamber and the microbubble blown at the immobilization chamber. The heat generated from chemical/biochemical reaction may result in the change of the temperature of the analytes inside the microbubble, thereby causing change of the frequency of optical resonance of the WGM optical resonator.

The present invention provides the ultrahigh temperature sensitivity of the WGM resonance for realizing calorimetric biosensors.

In some versions, the microchannel is made of PDMS, any soft polymer, 3-D printed plastic, silicon, ceramic, or any other biocompatible material which meets the design criteria for the construction of a sensitive calorimetric biosensor.

The microbubble in the calorimetric device can be the shape of a near spherical shell, a toroidal shell, a double walled shell, or a shell of any thickness and shape blown out using the planar glass blowing technique described here.

The microbubble in the calorimetric device may be constructed of any glass composition capable of softening in the temperature range of 0-2000° C. Examples include borosilicate glass, phosphosilicate glass, borophosphosilicate glass, aluminosilicate glass, and all forms of fused silica.

According to some versions of the chip-scale TAS, the microbubble may be formed not in a path of flow of the analyte or heat. A near spherical shell is an example of such a structure.

In some other versions of the chip-scale TAS, the microbubble may be formed in the path of a flow of the analyte or heat. Q-factors of the WGM resonator may be increased in this case. A torroidal shell is an example of such a structure.

BRIEF DESCRIPTION OF THE DRAWINGS

FIG. 1A is a schematic view of an on-chip double Archimedean spiral chromatography column with a bottom-side inlet and outlet;

FIG. 1B is a schematic view of the same chip integrated with two near spherical shells which can be used for inducing optical resonance;

FIG. 1C is a schematic view of a tapered fiber coupled to the spherical glass shell to achieve resonance based chemical detection;

FIG. 2A is a schematic view of a 500 μm thick silicon wafer;

FIG. 2B is a schematic view of the chromatography column with the inlet and outlet regions patterned and etched to a depth of 100 μm;

FIG. 2C is a schematic view of a 200 μm borosilicate glass wafer etched to create 50 μm etch pits using an RIE process;

FIG. 2D is a schematic view of the glass and silicon wafers aligned and anodically bonded at atmospheric pressure;

FIG. 2E is a schematic view of the glass wafer patterned and etched to result in 10-50 μm of remaining glass layer;

FIG. 2F is a schematic view of the wafer rapidly thermally annealed at 850° C. for 1 minute to blow out the etched regions;

FIG. 2G is a schematic view of inlet and outlet holes etched in the silicon wafer using DRIE process;

FIG. 2H is a schematic view of the entire silicon wafer etched in a wet etchant to result in glass bubbled wafer;

FIG. 5A is a view of a glass bubble on a silicon chip;

FIG. 5B is a schematic illustration of the bubble with various exemplary dimensions;

FIG. 5C is a graph of the glass bubble radius as a function of the membrane radius $r_0$;

DETAILED DESCRIPTION OF THE DRAWINGS

Figure 2A:
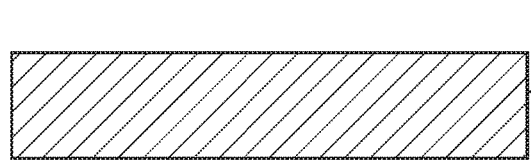
FIGS. 2A-2H is a schematic view of an exemplary fabrication process of a device in accordance with the present invention.

FIGS. 1A-1C are schematic illustrations showing the concept of a device according to an embodiment of the present invention. FIG. 1A shows an on-chip double Archimedean spiral chromatography column 102 with a bottom-side inlet 104 and outlet 106. FIG. 1B shows the same chip integrated with two near spherical shells 108, 110 which can be used for inducing optical resonance. One near spherical shell 108 is over the inlet 104. The other shell 110 is over the outlet 106. FIG. 1C shows a tapered optical fiber 112 coupled to the spherical glass shell 110 as a waveguide to achieve resonance based chemical detection. The column and the shells may be functionalized using PDMS or RTILs in a polymeric matrix.

Whispering gallery modes (WGMs) in optical cavities rely upon total internal reflection at the external cavity interface. Light is coupled into the microbubble through an evanescent wave from the tapered optical fiber 112 placed in close proximity of the microbubble resonator 110. Changes in the coupling of light to the microbubble resonator 110 can be quantified as changes in the intensity of the light measured by the photodetector 610 at the other end of the optical fiber as shown schematically in FIG. 6A.

TECHNICAL BACKGROUND

Whispering Gallery Modes: Considerations for Maximization of Chemical Sensitivity This section provides a background for the understanding of the optimization parameters for the glass microbubbles for sensing of the adsorbing analyte species on the functional coating on the inner surface of the bubbles.

A large refractive index contrast between the cavity within the microbubble and the surrounding medium strongly confines the WGMs and results in resonators with very high Q-factors. Conversely, a low refractive index contrast facilitates extension of the mode profile beyond the confines of the resonator medium allowing for the optical radiation to interact with the surrounding medium and thus allowing for a sensor design with exceptionally high sensitivity—albeit at the expense of the Q-factor. Optical resonators can be used for the realization of WGM based in-line sensors where an analyte gas interacts with the optical resonance through the inner surface of the cavity.

When interacting with vapor molecules, the functional coating layer (typically a polymer) undergoes a change in the refractive index (RI) and/or a thickness change which results in a spectral shift in the WGM [35, 36]. The sensitivity of the ring resonator S can now be written as $$S = \frac{d\lambda}{d\rho} = \frac{\partial \lambda}{\partial t}\frac{\partial t}{\partial \rho} + \frac{\partial \lambda}{\partial n}\frac{\partial n}{\partial t}\frac{\partial t}{\partial \rho} + \frac{\partial \lambda}{\partial n}\frac{\partial n}{\partial t} \quad (1)$$

where dγ/dρ is the WGM spectral shift due to the change of the analyte molecule concentration (ρ) in the polymer matrix upon exposure. On the right hand side in eq. (1), the first term quantifies the shift in the wavelength (λ) of the resonance due to a change in the thickness (t) of the polymer coating due to the adsorption of the analyte whereas the third term quantifies the spectral shift of resonance due to a change in the refractive index (n) of the polymer coating upon adsorption of the analyte molecules. The term in the middle represents the change in the refractive index (RI) of the polymer when the polymer swells/shrinks, i.e., RI change can be caused by either the polymer volume change induced upon adsorption of vapor molecules, or due to the doping effect of the vapor molecules in the polymer matrix [37]. A model for the expected sensitivity when the polymer is coated inside a cylindrical column has been reported by Sun and Fan [38]. Two cases can be considered: (i) RI of polymer coating is less than that of the glass shell (Low Index Polymer), and (2) RI of polymer coating is higher than that of the glass shell (High Index Polymer).

In case of a low index polymer, when the polymer RI is smaller than or close to that of the ring resonator, the polymer layer can be regarded as the extension of the ring resonator wall, regardless of the polymer thickness. Initially, when the polymer layer is thin, only the evanescent field exists in the polymer layer and the RI sensitivity is low. With the increased polymer thickness, higher order modes start to move inward, resulting in a higher RI sensitivity for those modes while the lower order modes are not affected much. The maximum value of $S_{RI}$ depends highly on the mode order. For example, $S_{RI}$ can reach approximately 600 nm/RIU (Refractive index units) for the $3^{rd}$ order mode, whereas it is nearly zero for the $1^{st}$ order mode. Furthermore, since light tends to localize near the polymer-glass interface, excessively thick polymer may not be beneficial in vapor sensing, as vapor molecules have to travel an additional distance to reach the maximal interaction with the light in the polymer. Thus, an optimal thickness of the polymer needs to be determined based on the RI sensitivity. For the WGM based vapor sensor, the wall thickness of the shell has a significant impact on the sensor performance. Here, the relative thickness between the wall and the polymer determines the modal profiles of the WGMs. As a result, the fraction of light and hence the RI sensitivity is lower with a thicker shell wall.

For high index polymers, the RI sensitivity of the above sensor structure is significantly different from the previous case. Here the sensitivity for the $1^{st}$ order mode increases monotonically with the increased wall thickness, whereas the sensitivity for the $2^{nd}$ and $3^{rd}$ order modes oscillates significantly. In particular, the sensitivity can be nearly zero at certain regions, where the mode possesses the dominant characteristic of the wall mode. After the de-coupling process, all modes approach their respective maximal sensitivity of the order of 1000 nm/RIU. Unlike in the low refractive index polymer, here the first order mode shows a high sensitivity since the mode is mainly confined within the polymer for thin layers. After the polymer mode intersects with the wall mode, the sensitivity drops to nearly zero since the mode is now confined to the shell wall. Meanwhile, the dominant polymer mode becomes the $2^{nd}$ order mode, which again has a high sensitivity. Finally it is seen that the thickness sensitivity $S_t$ gradually decreases to zero with increased polymer thickness for all modes. Thus, in the case of high RI polymers a thin layer with the mode confined towards the inside of the shell would be the most desirable thickness.

Detection Limit for Chemical Sensitivity Using WGM

The RI change due to the doping effect upon adsorption of the analyte by the polymer layer can be modeled by Lorentz-Lorenz equation [37] as $$\delta n = \frac{(n^2+2)^2}{6n} \frac{1}{3\varepsilon_0} (\delta \rho) \alpha \qquad (2)$$

Where $\alpha$ is the vapor molecule polarizability. Typically, the doping induced polymer RI change is always positive. However, thickness-related RI decreases when polymer swells. As a result, depending on the ring resonator sensor configuration and the target vapor analyte, a negative sensitivity may occur, which causes the WGM to shift to a shorter wavelength upon detecting chemical vapors. This phenomenon has been experimentally observed in optical resonator vapor sensor [39], and can provide an additional chemical differentiation capability.

The limit of detection (LoD) of the ring resonator vapor sensor can be determined by its sensitivity and its minimal resolvable spectral shift $(\delta \lambda)_{min}$ i.e., LoD=$(\delta \lambda)_{min}$/S, where $(\delta \lambda)_{min}$ is typically chosen to be $\frac{1}{20}$-$\frac{1}{50}$ of the WGM resonance linewidth. The linewidth is inversely proportional to the ring resonator's Q-factor which is given by $$Q = \frac{2\pi n}{\lambda \sigma \eta} \qquad (3)$$

where $\eta$ is the fraction of light in the polymer and $\sigma$ is the polymer's optical attenuation coefficient. It is now evident that there is clearly a trade-off between the polymer thickness which may improve $S_{RI}$ however it may still degrade the LoD due to the large attenuation coefficient as compared to the glass/silica shell walls. Using a polymer layer of 1 µm thickness, RI of 1.47, $\sigma$=0.23 cm$^{-1}$, Q=1×10$^6$ for $\lambda$=760 nm, $\eta$=50%, $n_{shell}$=1.45, and using eq. (3), a resolution of $\frac{1}{20}$ of resonance linewidth results in a spectral linewidth resolution of ≤0.05 µm. However, due to temperature induced fluctuations this will likely to be limited to ~0.1 µm. Under these assumptions and an expected sensitivity S of 600 nm/RIU, the LoD can be estimated to be 1.7×10$^{-7}$ RIU. Equation (2) relates the RI change in the polymer layer to the vapor molecule density in the polymer matrix, which is in turn related to the vapor concentration in free space, $\rho_0$, by the partition coefficient K=$\rho/\rho_0$, with value of K ranging from a thousand to hundreds of thousand [40]. Using K=1000 and $N_A \alpha/(3\varepsilon)$=30 cm$^3$/mol (NA is the Avogadro's number), which are typical for many types of vapor molecules, we have $\delta(n)$=2.4×10$^{-6}$ RIU/ppm at room temperature and the atmospheric pressure. Using the LoD of 1.6×10$^{-7}$ RIU for RI, we obtain a concentration LoD of 70 ppb for chemical vapors [38]. This is a highly promising value for detection of components in a chromatography column.

WGM Based Sensor Response Time

As discussed above, the sensitivity and the LoD were deduced based on the assumption that the analyte molecules are fully adsorbed uniformly by the polymer layer inside the shell and reaches equilibrium with the polymer. However for rapid vapor detection, especially for gas chromatography, the diffusion time for vapor molecules to reach the location in the polymer where the WGM mode is confined needs to be accounted for. Typically, the diffusion constant for vapor molecules is on the order of 10$^{-10}$-10$^{-12}$ cm$^2$/s [37] and can take tens of seconds for the detection signal to achieve its saturation value [37]. Looking at the chromatogram shown in FIG. 4(f) this may be sufficient for the resolution of several of the heavier components in simulated distillation separation. However, this would be insufficient for the resolution of the first few components of the mixture. In such as case the sensitivity may have to be optimized against the time constant through the use of a thinner polymer layer. For example, if the polymer thickness is reduced to 0.5 µm from 1 µm, the diffusion time will be shortened by 4 times, but in the meantime, the RI sensitivity presented earlier will drop to 200 nm/RIU from 400 nm/RIU for low refractive index polymer. An alternative strategy could be the use of a high RI polymer where for the same thickness of 0.5 µm thickness, a RI sensitivity of nearly 600 nm/RIU may be achieved under the assumption that the diffusion constant remains unchanged. Another option is to use a polymer with a high partition coefficient so as to achieve a higher vapor density in the polymer matrix.

Temperature Sensitivity of WGM and Calorimetric Biosensing

As we have seen WGM resonance frequencies depend on the size and refractive index of the resonator. A small change in the size or the refractive index can cause a significant resonance frequency shift for a given mode. Since both the refractive index and the size of a spherical shell depend upon temperature due to thermo-optic and thermal expansion effects, a WGM resonator can be configured as a sensitive thermometer. Assuming a WGM circulates around the equatorial plane of the glass bubble, the resonance in an azimuthal mode m, can be given by $$2\pi r_g = m\lambda/n_{eff} \quad (4)$$

where $\lambda$ is the resonance wavelength, $2r_g$ and n are the diameter and the refractive index of the resonator respectively. Assuming a linear dependence of thermal expansion and refractive index on temperature for small temperature variations, these can be expressed as $dr_g/r_g = \alpha dT$ and $dn/n = \beta dT$; where $\alpha$ and $\beta$ are the thermal expansion coefficient and thermo-optic coefficient respectively. Taking a variation of eq. (4), can express it as $$dn/n + dr_g/r_g = d\lambda/\lambda \Rightarrow d\lambda/dT = (\alpha+\beta)\lambda \quad (5)$$

Since the magnitude of the wavelength shift is much smaller than the resonance wavelength in the testing temperature range, we can use the measured resonance wavelength at a reference temperature (such as room temperature) to calculate the temperature sensitivity for a silica micro-bead operated at a given resonance mode and regardless of the exact radius of the micro-bead, the average value of $d\lambda/dT$ is found to be ~13.89 μm/K. Thus, for a resonator with resonance wavelength of 760 nm this corresponds to an ideal resolution of ~20 μK. However, accounting for all the thermal fluctuations and measurement bandwidths used in a typical experimental set-up these resonators will be capable of a resolution of ~1 mK or better [41].

The Device and Method

An integrated chromatography chip with a microbubble-based optical resonator for gas discrimination is provided. The ultimate goal will be to discriminate 5-10 component gas mixtures containing volatile organics. Furthermore, a calorimetric biosensor for the detection of bioanalytes of interest such as creatinine is designed and implemented.

Monolithic Fabrication of an Integrated Chromatography-Microbubble Column

Figure 2B:
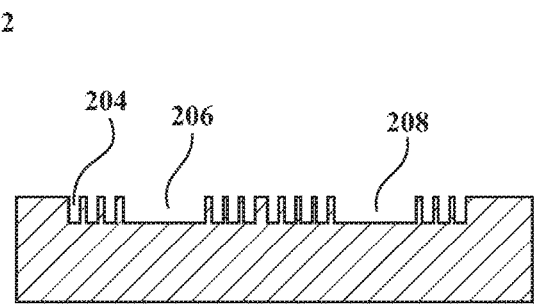
Figure 2C:
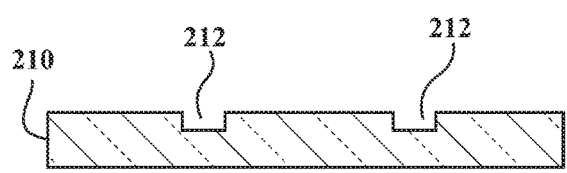
Figure 2D:
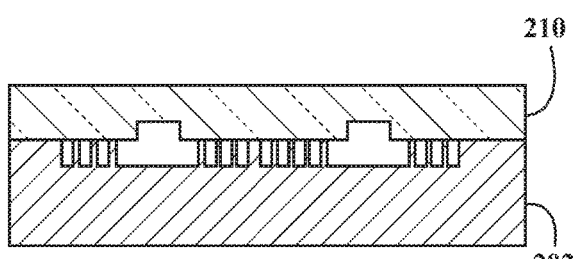
Figure 2E:
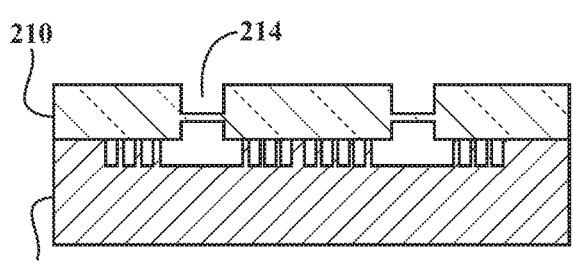
Figure 2F:
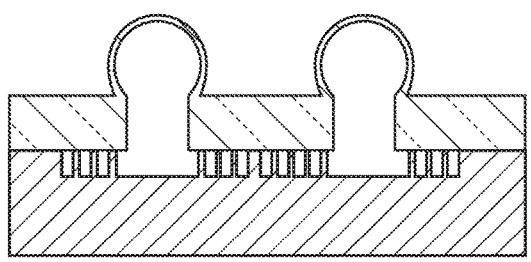
Figure 2G:
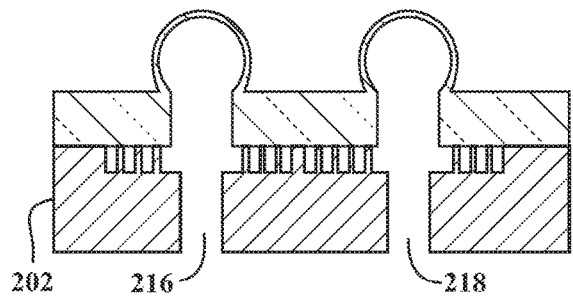
Figure 2H:
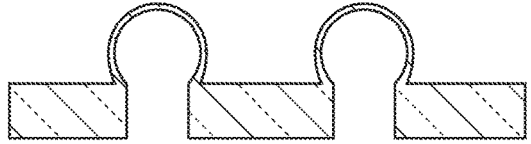

An exemplary embodiment of the fabrication process of a monolithically integrated microfluidic device comprising a chromatographic column for volatile organics separations and microbubble based WGM resonators for the detection of the components is schematically illustrated in FIGS. 2A-2H. The process starts with a 500 μm thick silicon wafer 202, as shown in FIG. 2A. As shown in FIG. 2B, the chromatography column 204 with the inlet 206 and outlet 208 regions are patterned and etched to a depth of 100 μm. In FIG. 2C, 200 μm borosilicate glass wafer 210 is etched to create 50 μm etch pits 212 using RIE process. In FIG. 2D, the glass 210 and silicon 202 wafers are aligned and anodically bonded at atmospheric pressure. As shown in FIG. 2E, the glass wafer 210 is patterned and etched to result in 10-50 μm of remaining glass layer. In FIG. 2F, the wafer is rapid thermal annealed at 850° C. for 1 minute to blow out the etched regions. Finally, inlet 216 and outlet 218 holes are etched in the silicon wafer 202 using DRIE process, as shown in FIG. 2G, or the entire silicon is etched in a wet etchant to result in a glass bubbled wafer, as shown in FIG. 2H.

According to an embodiment of the present invention, a mixture of gas analytes enter the inlet 104 of the chromatography column 102. Each component of the mixture is separated by the chromatography column and exits the outlet 106 and fills the microbubble 110 at different times. A light, such as a laser light, coupled into the waveguide 112 will generate an optical resonance in the microbubble 112. The resonance frequency is dependent on the type of the gas component and its interaction with the polymer coating of the microbubble, since the reaction between the component of the gas analytes and the polymer coating changes the refractive index of the interface of the microbubble. In this embodiment, the microbubble is not located in the flow path of the gas analyte. The density of the gas analytes in the microbubble may be low since the gas analytes in the microbubble is due to diffusion from the chromatography column.

Figure 10:
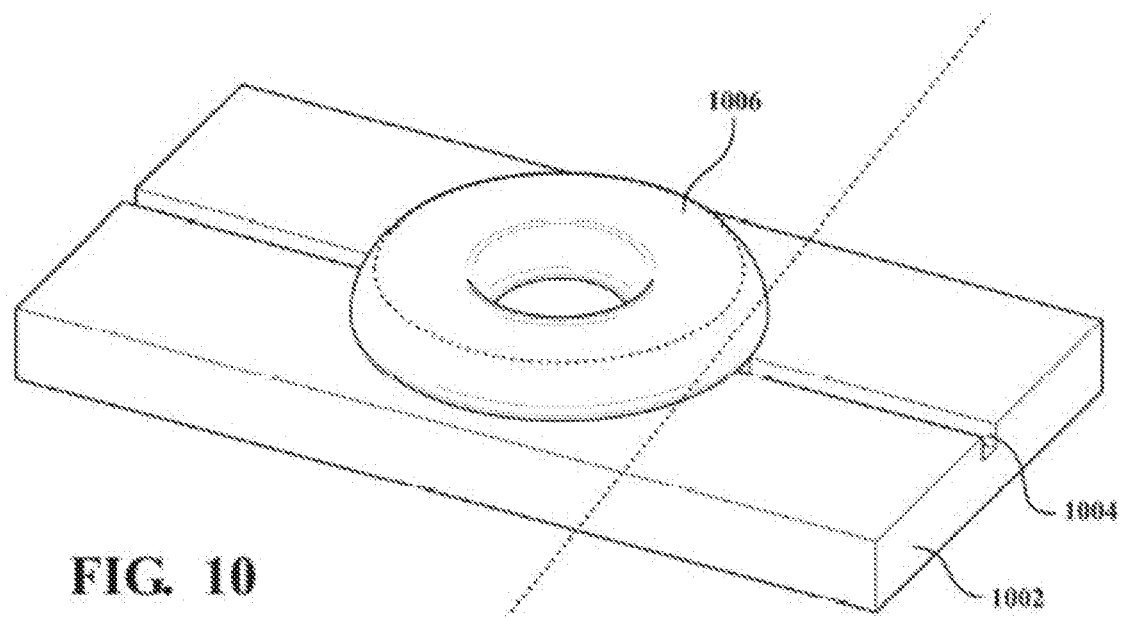
FIG. 10 is a schematic illustration of a micro-toroidal bubble formed on a chip.
Figure 11A:
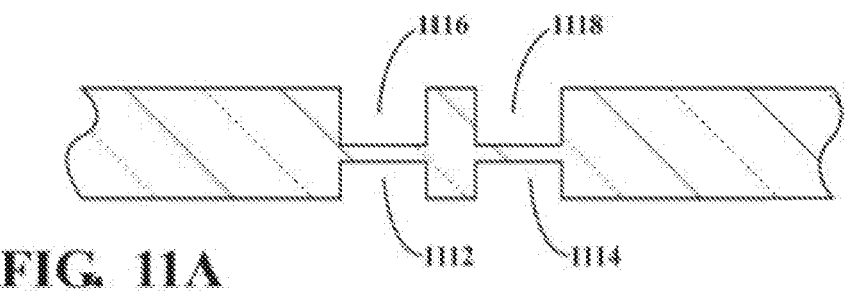
FIG. 11A is a schematic view of a glass wafer patterned and etched to form a toroidal structure.
Figure 11B:
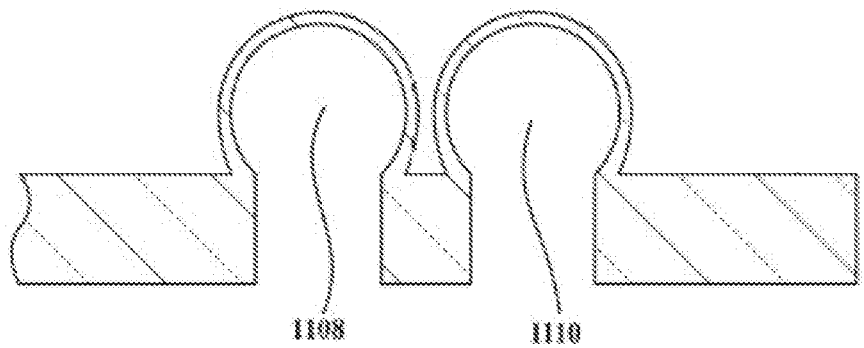
FIG. 11B is a schematic view of a glass wafer rapid thermal annealed to blow out the etched regions forming a toroidal structure.

In another embodiment, during the fabrication process, the etched feature 214 in FIG. 2E may be a feature as shown in FIG. 11A. Instead of etching one pit 214, a ring is etched, the cross section of which is shown by 1116 and 1118 on the top, 1112 and 1114 on the bottom. During the rapid thermal annealing step, a toroidal structure is formed, resulting in a structure similar to the structure 1006 shown in FIG. 10. In FIG. 10, a channel 1004 is formed on the wafer 1002.

In this embodiment, the toroidal microbubble is displaced in the flow path of the gas analyte. The gas analyte from one part of the channel of the chromatography column beneath 1108 goes through the microtoroid before exiting from the other part of the channel of chromatography column beneath 1110. Therefore, the density of the gas analyte in the microtoroid is similar to the density of the gas analyte in the chromatography column.

We have recently developed an RIE process that allows for high-aspect ratio anisotropic etching of glass substrates with rates of over 1 μm/min [42]. This capability will provide us with the flexibility of creating glass regions with thicknesses in the 10-50 μm range as required so as to be able to create near spherical glass bubbles of diameters ranging from 50 μm-≥500 μm. Furthermore, at the end of the process, the wafer will be diced into individual devices. At this stage the devices can be processed to create inlet and outlet holes to realize the integrated chromatographic device or the entire silicon substrate can be etched away in hydrofluoric-nitric-acetic acids or plasma etch to create glass bubble chip which will be used for calorimetric biosensor device as will be explained later. The fabrication process will use only three mask steps with double side alignment to achieve the bubble structures. In one exemplary embodiment, the double Archimedean spiral geometry is used for the chromatography column with 2 m length as described in our previous work [26]. Considerable optimization will be required to achieve good anodic bonding in the chromatography column region since these regions will also be subjected to the high temperature and pressure during the bubble formation process. These regions will have much thicker glass ~200 μm and will not bubble up as the thinned regions. This will have to be optimized based upon the preliminary results obtained, which will be described in "PRELIMINARY RESULTS" section. For the initial demonstration of the device, a film of nonpolar Polydimethyl siloxane (PDMS, 2% vinyl) (OV-1) containing 2% vinyl, 0.737 g/ml, in a pentane solution, may be used as dynamic coating of the chromatography column and one of the two glass bubbles. A dynamic coating procedure may be used to deposit the stationary phase. The column and the bubbles may be initially filled with a solution of pentane to remove any impurities. The pentane may then be removed by purging with nitrogen gas. Next the PDMS solution is infused into the column at a rate of 2 µl/min using a syringe pump. Once the inlet bubble and the column is entirely filled, the outlet may be connected to a nitrogen tank and the PDMS/Pentane solution may be pushed out of the column by applying a pressure to cause a controlled evacuation rate of the coating solution (ca. 20 psi), thereby leaving a thin film of liquid PDMS stationary phase. Once all excess coating solution has been evacuated, the nitrogen flow may be allowed to continue for approximately 30 min at 10 cm/s to evaporate any residual solvent. The device may then be thermally conditioned to achieve vinyl cross-linking by placing them into a GC system, and establishing He flow through the column. The temperature of the GC may then be programmed to rapidly raise it to 250° C. to initiate the cross-linking reaction, and may be held at this temperature for 1 h. Leaving one of the glass bubble clean without any PDMS may allow functionalization with other polymers in that bubble allowing for evaluation for WGM based sensing.

Functional Polymer Evaluation

Initially, the chromatography column may be benchmarked for column efficiency by connecting the output of the column to a commercial GC flame ionization detector. Chromatograms consisting of n-heptane, n-hexane, and n-octane mixture may be used for initial benchmarking. The number of theoretical plates (N) the µGC column possesses may be determined using the expression $$N = 5.54 \times \left(\frac{t_r}{\sigma_{0.5}}\right)^2 \quad (6)$$

where $\sigma_{0.5}$ is the full width at half maximum and $t_r$ is the retention time. The plate height or the height equivalent to a theoretical plate (HEPT) is obtained using the column length, L, and from the expression HEPT=L/N. The separations may be performed at multiple linear velocities of the helium carrier gas to generate Golay plots and may be fitted using the Van Deemter equation for plate height. From the experimentally obtained values of $t_m$ (mobile phase transit time through the column) and $t_r$ (the retention time of each analyte), the retention factor k' will be calculated using the expression.

$$k'=(t_r-t_m/t_m) \quad (7)$$

The values of $t_r$ and $t_m$ may be obtained from the chromatograms for the various flow velocities. All these measurements may be made using an Agilent 7890 gas chromatograph equipped with an FID detector available at Penn State through shared facilities. We may initially benchmark the PDMS coated column and then evaluate the performance of a recently developed polymer template comprising of highly aromatic sulfonated poly(arylene ether sulfone)s with 1,3, 5-s-triazin ionomer, abbreviated as DPA-PS:BP (1:1), and have it combined with various ionic liquids as the receptor material as both the stationary phase of the chromatography column and as the sensing material for WGM resonator. DPA-PS:BP provides much improved swelling capacity for RTILs up to 300 wt % while keeping relatively high elastic modulus (e.g. 600 MPa for 300 wt % RTIL uptake) [24]. Because of the enhanced uptake values, the polymer/RTIL film is expected to exhibit enhanced sensitivity [25]. The thickness of the receptor material primarily determines the surface area to volume ratio of the material and in turn is expected to affect the achievable response time and interaction sensitivity. In this context the use of a high RTIL uptake polymer is advantageous since the polymer essentially determines the film thickness over a wide range RTIL doping. The ionomer solution may be diluted as required in N-methyl 2-pyrrolidone (NMP) solvent. Furthermore, DPA-PS:BP (1:1)-based ionomers are capable of operation at high temperatures of up to 400° C. [43] and can therefore provide critical high temperature operation flexibility for high temperature chromatography applications [44]. However, if this material proves to be ineffective for chromatography separations, then we may use PDMS based column coating followed by DPA-PS:BP (1:1) polymer coating only for WGM sensing where the RTIL functionality is expected to provide the required selectivity to the various volatile organics.

As described in the technical background, we may perform extensive optimization between the glass shell wall thickness, and the functional polymer coating thickness and composition to obtain the WGM response to the various organic vapors. This may provide us with a greater understanding of the interaction between the vapors and PDMS or RTIL-based ionomer functionalization. As discussed earlier, in order to obtain the greatest sensitivity and response speed, we need to optimize the thickness of the coating such that WGM modes are sustained in the polymer as well as being concentrated at the inner face of the polymer such that the vapors are able to rapidly diffuse into this layer. At this time there are no detailed optical properties of the DPA-PS:BP (1:1)-based ionomers available. We may make thin films of the ionomer doped with various RTIL's and perform ellipsometric measurements to obtain the refractive index of this family of materials in the 760 nm wavelength region. This may allow for accurate modelling and understanding of the functioning of the devices.

Integrated WGM Resonator

Figure 3A:
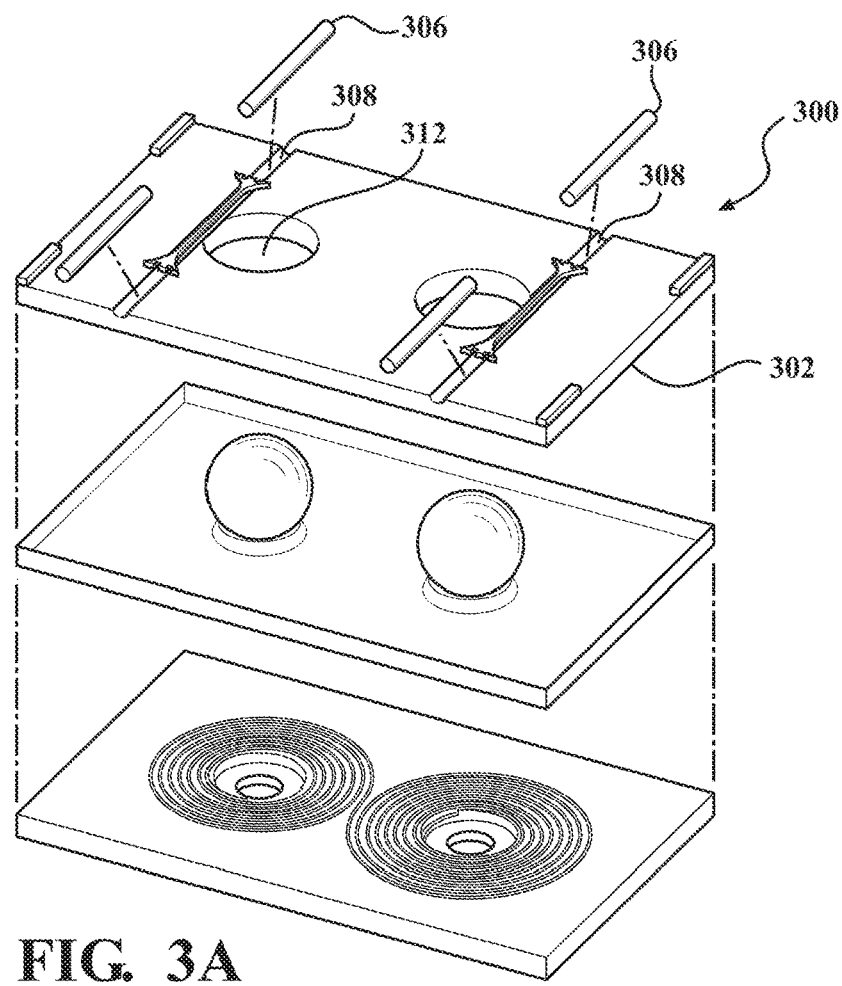
FIG. 3A is an exploded schematic illustration of a 3-wafer integrated WGM resonator device including a freestanding silica waveguide structure.
Figure 3B:
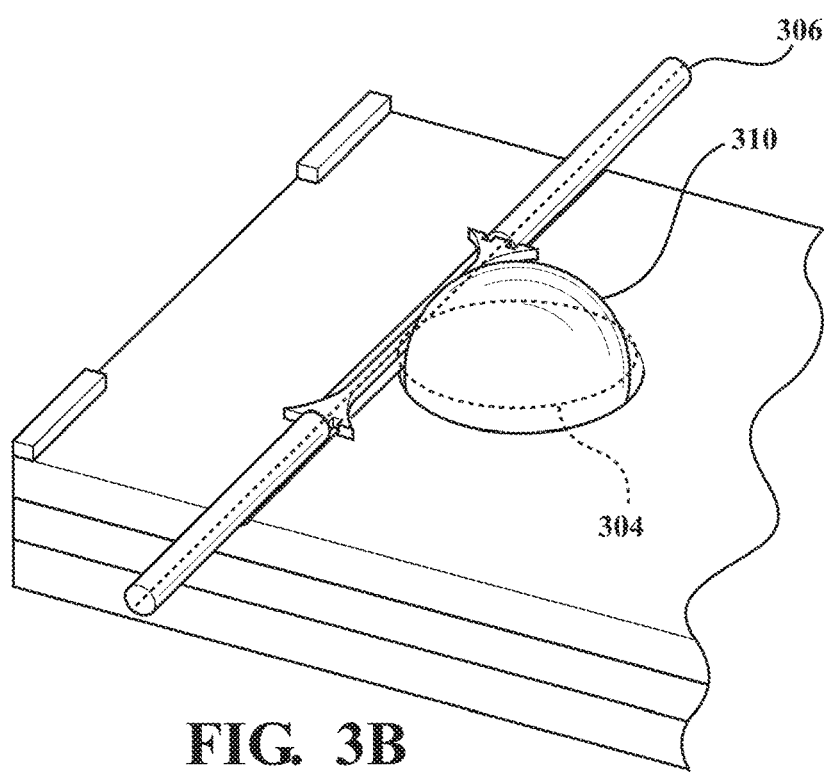
FIG. 3B is a schematic illustration of a self-aligned fiber configuration that allows for an integrated optical device where light can be robustly coupled to a fiber pigtail and positioned using pre-aligned V-groove channels.
Figure 3C:
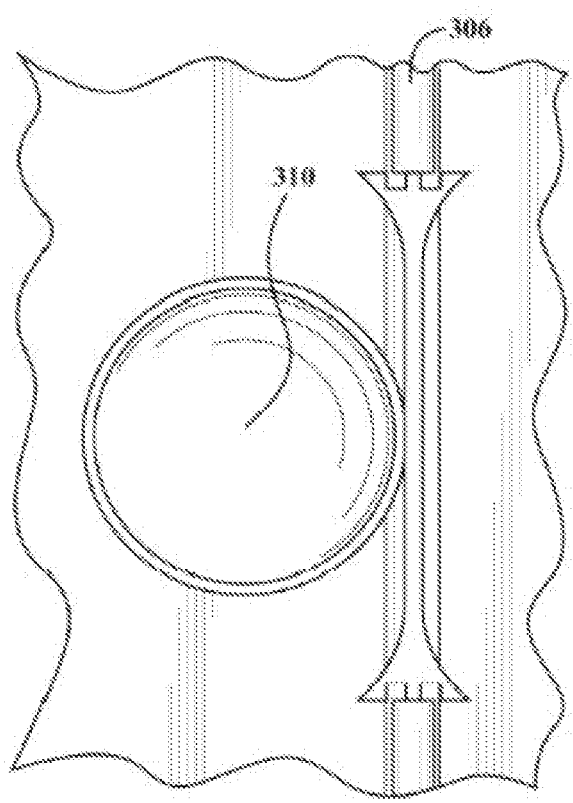
FIG. 3C is a top view of the integrated optical device with the bubble and aligned fiber in place.

In one embodiment, the device uses the silicon-glass two wafer stack. In this arrangement, the tapered optical fiber may be manually positioned and adjusted to achieve critical coupling of the evanescent wave into the glass shell. This method is not suitable for portable devices where such elaborate positioning arrangements will not be possible. In order to achieve an integrated device with the pre-aligned fiber waveguide configuration, a third wafer may be used as shown schematically in FIG. 3A. FIG. 3A is a schematic illustration of a 3-wafer integrated WGM resonator device including a freestanding silica waveguide structure 300. An oxidized silicon wafer 302 with a 10 µm thick silicon oxide may be used. The thickness of the silicon wafer 302 may be pre-determined so as to place the oxide layer at the equatorial plane 304 of the bubbles blown when the three wafer stack is bonded together as shown in FIG. 3B. The self-aligned fiber configuration achieved allows for an integrated optical device where light can be robustly coupled to a fiber pigtail 306 and positioned using pre-aligned V-groove channels 308. FIG. 3C shows the top view with the bubble 310 and the aligned fiber 306 in place. A through hole 312 in the wafer 302 may be etched using DRIE process so as to allow for the glass microbubble to be able to pass through.

Coupling light from optical fiber to an on-chip waveguide may result in high losses due to mode-size and effective-index mismatch between the optical fiber and the silica waveguide structure, which can induce optical scattering and back reflection. Tapering from the waveguide dimensions to the fiber mode dimensions may be used for improving coupling efficiency between optical-fiber and waveguide modes on the silica structure as schematically shown in FIG. 3B [45, 46]. However, to avoid excessive coupling to radiation modes in the taper, the required typical taper length must be of the order of a millimeter. Inverse tapers, decreasing the waveguide width at the end, accomplishes low loss coupling by expanding the waveguide mode to match the fiber mode size. Almeida suggested a micrometer-long nanotaper coupler that converts both the mode size and the effective index of the waveguide to that of the optical fiber [47]. In this coupling scheme, the optical fiber has to be no more than a few micrometer away from the tapered waveguide end. The oxide layer may be patterned to result in an overhanging silica waveguide running tangential to the spherical shell as shown in FIG. 3B. In order to better fix the optical fiber in the optimum position for the best coupling, a support structure may be used. In one embodiment, V-grooves may be etched into our chip to be able to actively align and securely attach the optical fibers in the optimum optical coupling position with UV curable epoxy. Since the mode size and effective index of the taper strongly depend on the surroundings of the nanotaper we may use an overhanging silica nanotaper in air, avoiding the possibility of increased losses into the nearby substrate. The V-groves for the silica waveguide as well as for the placement of the pigtail fibers may be accomplished using anisotropic wet etchants of silicon. A V-grove channel may be etched in the silicon wafer using KOH-based crystallographic silicon etchants which will allow for easy alignment of pigtail fiber by placing the fiber into the V-grove and attaching using ultraviolet curable epoxy.

One other issue that can result in a lossy performance can be the surface roughness related losses in the integrated glass waveguide due to the roughness associated with etching and lithographic definition of the structure. This can be overcome by performing a $CO_2$ laser based rapid reflow process which will both result in a smooth surface and potentially optimize the cross-sectional shape (e.g., cylindrical waveguide) to reduce loss, and improve mode matching to result in increased coupling efficiency. Finally, the third wafer with the optical waveguide fiber may be attached to the spherical shell wafer using thermally curable epoxy—this will allow for the accurate placement of the fiber in relation to the spherical shell structure which will be critical for achieving strong coupling between the shell and the fiber. These steps may be performed using the Finetech FIN-EPLACER® die bonder which allows for 3D assembly and placement with an accuracy of 1 µm. The use of thermally curing epoxy may allow for any fine adjustment of the waveguide chip before being cured in place.

WGM Based Calorimetric Biosensor

Figure 4:
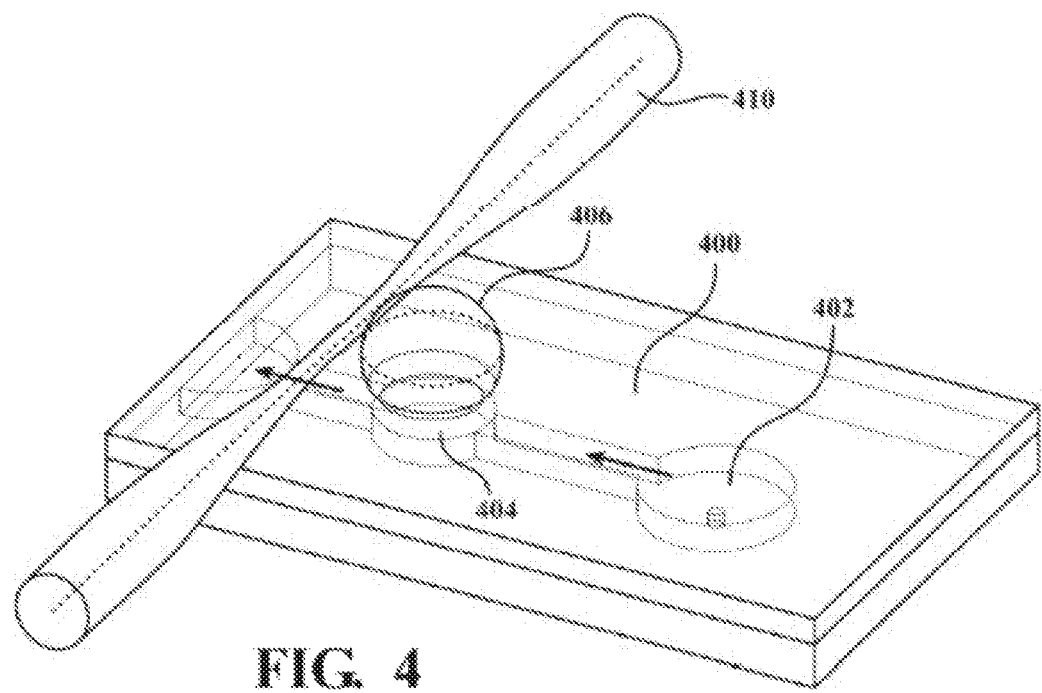
FIG. 4 is a schematic illustration of the calorimetric biosensor using the glass microbubble WGM and immobilized enzymatic reaction for the detection of an analyte.

Our recent work on remote calorimetric creatinine sensor using immobilized enzymes in commercially available KAPTON® mm-sized tubing has shown that it is possible to obtain resolution of ~1 mM for creatinine using the enzyme creatinine deiminase and ≤1 mM for urea using the enzyme urease. One drawback of this sensor configuration was the less than perfect transfer of heat from the KAPTON® tubing to the quartz resonator sensor. The device can inherently address this drawback and can result in further reduction in the sample sizes of the analyte. To realize this device, we may create a mold in a silicon wafer and use it to mold PDMS to create the fluidic channels and the reactor pit as shown in FIG. 4. The PDMS mold may consist of an inlet chamber 402 followed by the reaction chamber 404 in which the enzyme may be immobilized. The entire volume of the chamber may be in the nanoliters. A glass bubble chip 400 with a microbubble 406, diced to the right size and fabricated using the process described earlier, may be obtained by etching away all the silicon in wet or plasma etching. Creatinine deiminase enzyme immobilized using alginate bead method [48] may be freshly prepared and placed in the reactor chamber of the PDMS. The PDMS surface may be oxidized with the discharge from a Tesla coil. This corona discharge in air produces chemical species which react with the PDMS surface to convert it to a less hydrophobic surface and improves the adhesion to the glass surface. The glass bubble chip may be attached to the PDMS fluidic column as shown in FIG. 4.

The device may be placed in proximity to a tapered fiber 410 and the optical resonance may be obtained. Thereafter, the PDMS channel may be pumped with buffer solution to obtain the shift due to the bubble being filled with the phosphate buffer solution. Creatinine solution of known molarity may be prepared and may be pumped through the chamber. As the analyte interacts with the immobilized enzyme, the small volume of the fluid in the glass microbubble will heat up and consequently a shift in the resonance frequency due to the change in the temperature will be obtained. The enthalpy of the oxidation of creatinine was experimentally measured to be 94 kJ/mol [33, 48]. Thus for a 10 µM solution and the shell volume of 220 nl, corresponding to a 750 µm diameter spherical shell, the reaction will result in a temperature increase of the analyte by ~0.22 mK, assuming the specific heat of the analyte to be that of water. This temperature rise can be easily detected by the WGM resonator which is capable of 50 µK temperature resolution. Thus, the WGM resonator is expected to provide unprecedented analyte detection capability. While we focus on creatinine sensing in this work, the device may be capable of detecting any bioanalyte for which a corresponding enzyme can be immobilized.

Preliminary Results

Chip-Scale Glass Blowing

FIG. 5A shows a near spherical glass bubble blown on a silicon chip using microfabrication techniques. The process uses the highly temperature dependent viscosity of glass to form these materials into the proposed shapes. The glass is heated above its softening point, which occurs at 821° C. for PYREX® 7740 glass. To fabricate spherical structures, the silicon wafers are patterned using photoresist and are etched using deep silicon etching process to realize cylindrical and annular cavities. The patterned silicon wafer is then anodically bonded to borosilicate glass wafers. The glass wafer is subsequently thinned to 10-50 µm in thickness to result in a highly polished and smooth surface finish using wet or dry etching methods. The wafers are typically bonded at atmospheric pressure and the subsequent high temperature process results in a convex curved shell-like structures. The wafers are quickly heated in a rapid thermal anneal process at atmospheric pressure and brought to ambient temperature rapidly, which ensures that the glass solidifies before the pressure inside the shells changes due to the lowering of temperature. The stresses that are built in through this process can be reduced by annealing the structures for about an hour below the strain point of the glass. As illustrated schematically in FIG. 5B, the final height, $h_g$, the hemisphere develops is a function of the furnace temperature $T_f$, the temperature at which the cavity is sealed $T_s$ (both given in Kelvin) and the depth $h_e$ and radius $r_0$ of the etched cavity in the silicon wafer and is given by [22]:

$$h_g = \frac{\left[(3V_g + \sqrt{r_0^6\pi^2 + 9V_g^2})\pi^2\right]^{2/3} - r_0^2\pi^2}{\pi\left[(3V_g + \sqrt{r_0^6\pi^2 + 9V_g^2})\pi^2\right]^{1/3}} \text{ where} \quad (8)$$

$$V_g = h_e\pi r_0^2\left(\frac{T_f}{T_s} - 1\right)$$

which the radius, $r_g$, of the glass spherical shell can be calculated as $$r_g = \left(\frac{h_g^2 + r_0^2}{2h_g}\right) \quad (9)$$

and is plotted in FIG. 5C as a function of the radius of the membrane or etched pit in the silicon substrate.

Whispering Galley Mode Resonance in Micro Glass Bubbles

Figure 6A:
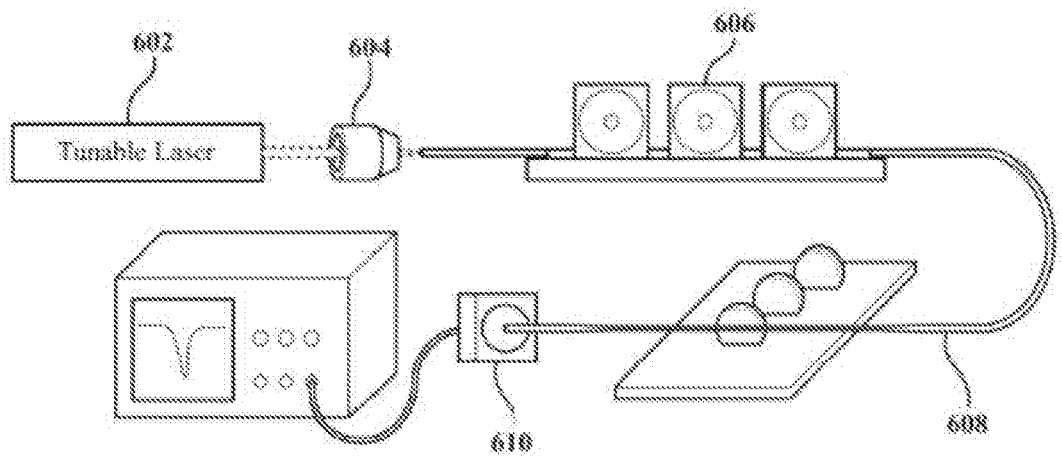
FIG. 6A is a schematic illustration of an experimental set-up for the measurement of the WGM resonance in glass bubbles.
Figure 6B:
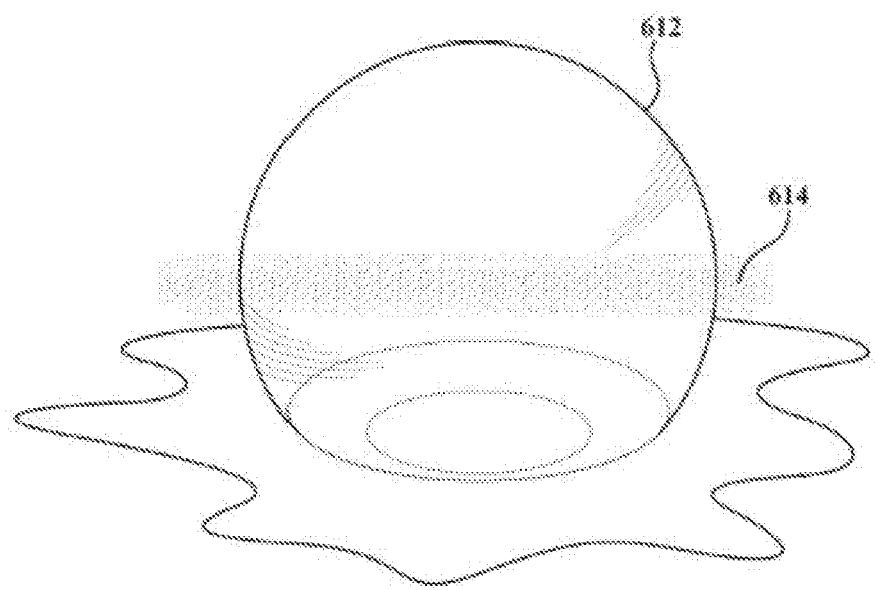
FIG. 6B is a schematic illustration showing light confined to an equatorial plane of the bubble upon evanescent coupling of the light through the tapered fiber.
Figure 6C:
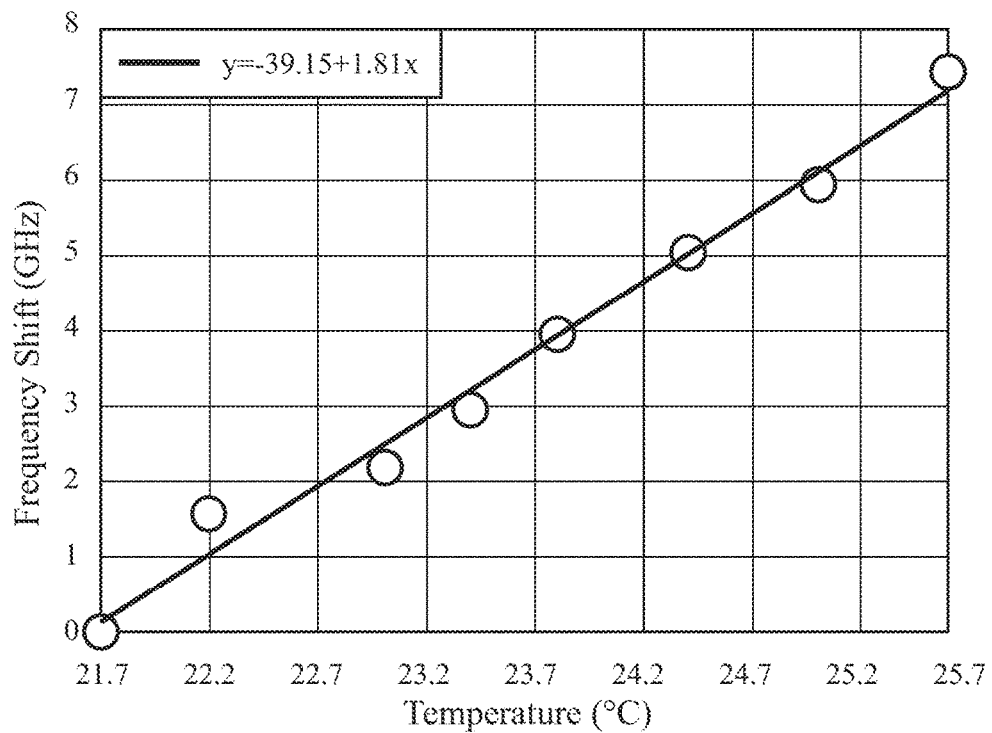
FIG. 6C is a graph showing the temperature dependence of one of the resonance modes of the resonator.
Figure 6D:
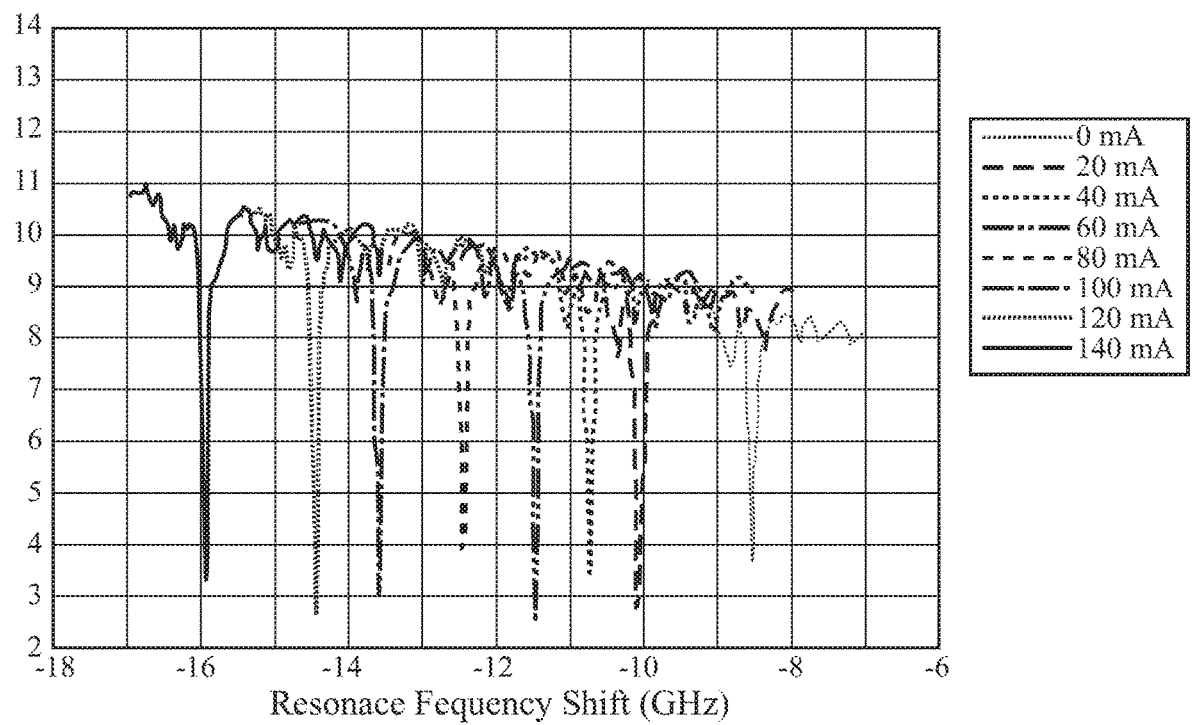
FIG. 6D is a graph showing the temperature dependent shift of one of the modes of resonance.

Preliminary experiments on the suitability of the glass bubbles blown on a silicon chip from BOROFLOAT® glass for WGM resonance have been performed. Initially, no optical resonance was obtained since the bubbles had more of a hemispherical shape with the equatorial plane located on the substrate than above it. This situation was remedied by changing the fabrication process which included etching of the glass wafer in the bubble region followed by a rapid thermal anneal step in vacuum rather than at ambient pressure. This allowed for the formation of the near spherical glass bubbles as shown in FIG. 5A. The thickness of the spherical shells can be tailored from a few hundred nanometers to 5 μm. The experimental set-up used for characterizing optical resonance in the glass bubble is shown in FIG. 6A, including a tunable laser 602, objective lens 604, waveplates 606, a fiber taper 608 coupled to a microbubble on a chip and a photodiode 610. Using a 760 nm tunable laser 602, optical resonance with Q of up to ~17 million may be achieved in these bubbles. FIG. 6B shows a glass bubble 612 with resonance mode in which the light 614 is clearly confined to the equatorial plane of the bubble. The sensitivity of the bubble to physical input was measured by changing the temperature of the bubble. As seen in FIGS. 6C and 6D, the resonance frequency increases with increasing temperature and exhibits an extraordinary sensitivity of 1.56 GHz/° C. allowing for ≤50 μK temperature sensitivity.

Double Archimedean Spiral Gas Chromatography Column

Figure 7A:
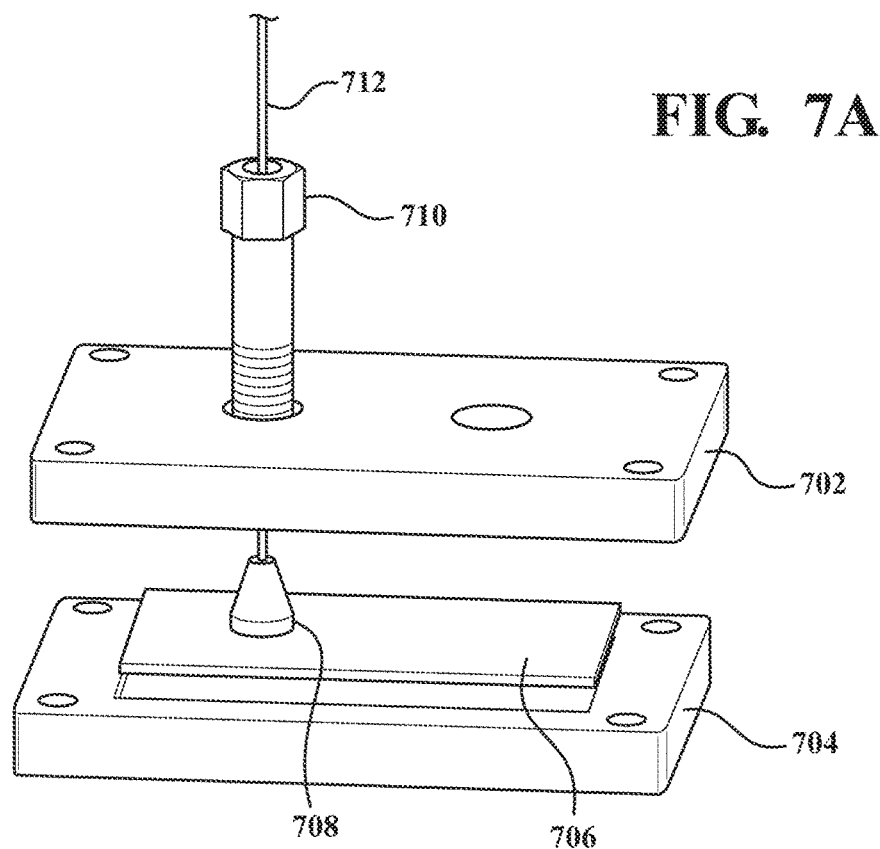
FIG. 7A is an exploded view of an assembly of a 2 m long μGC column on a silicon chip using a graphite ferrule for high temperature separations.
Figure 7B:
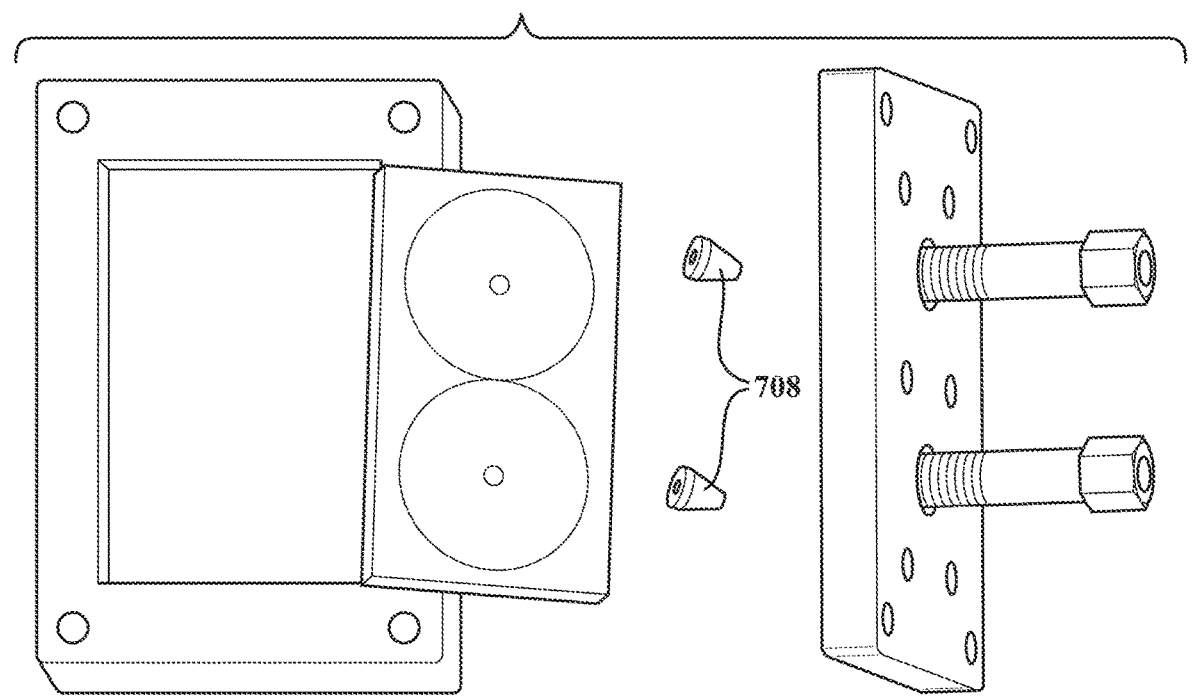
FIG. 7B is a disassembled view of the assembly of the 2 m long μGC column on a silicon chip using graphite ferrules for high temperature separations.
Figure 7C:
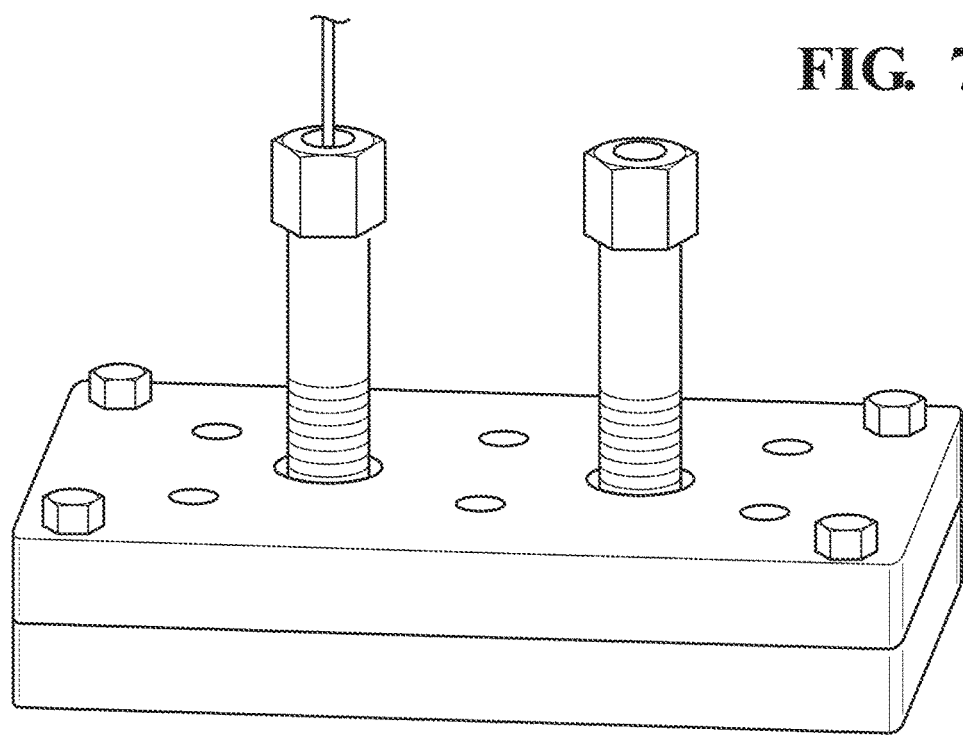
FIG. 7C is an assembled view of the assembly of the 2 m long μGC column on a silicon chip using graphite ferrules for high temperature separations.
Figure 7D:
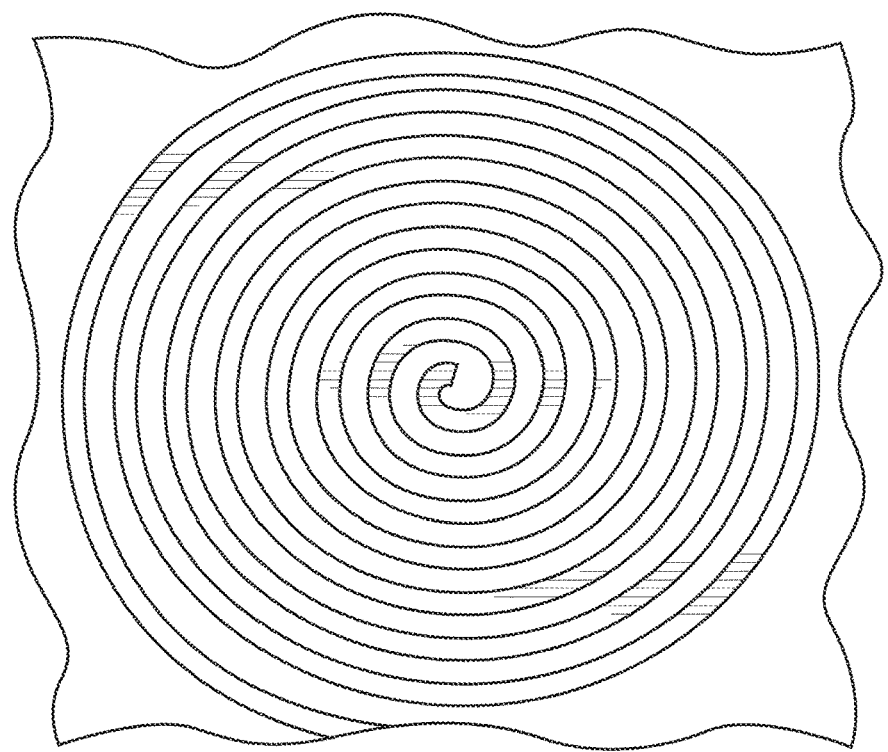
FIG. 7D is a drawing of a SEM image of the μGC column showing the Archimedean spiral.
Figure 7E:
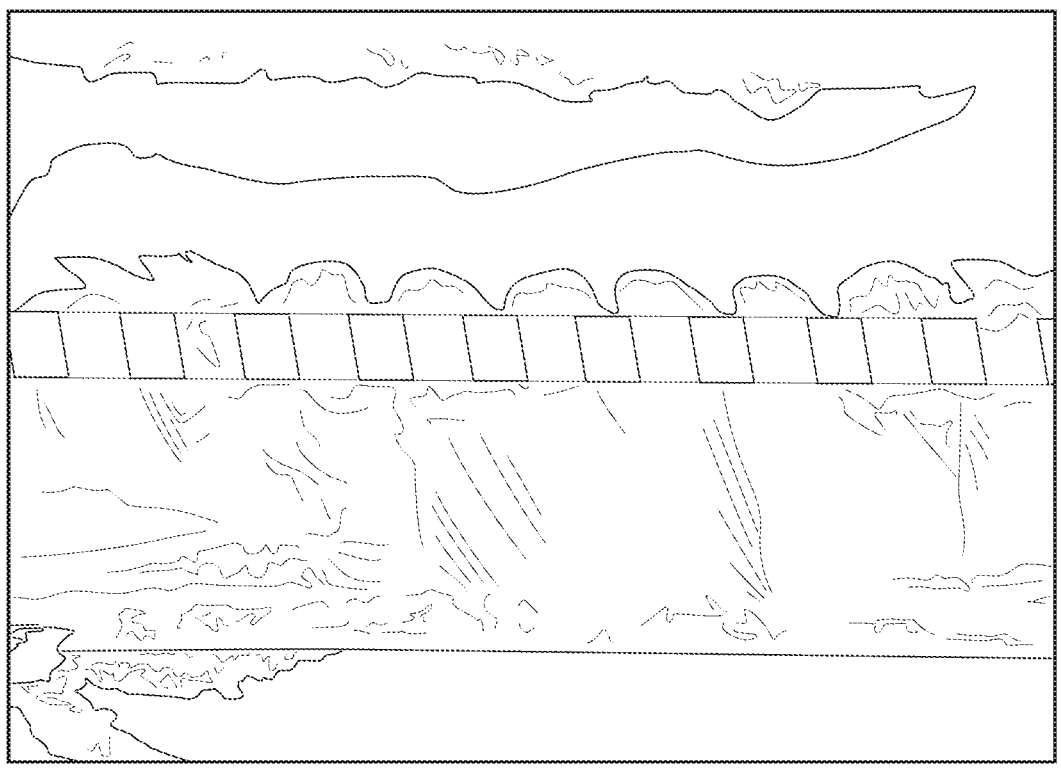
FIG. 7E is a cross-sectional image of the μGC column.
Figure 7F:
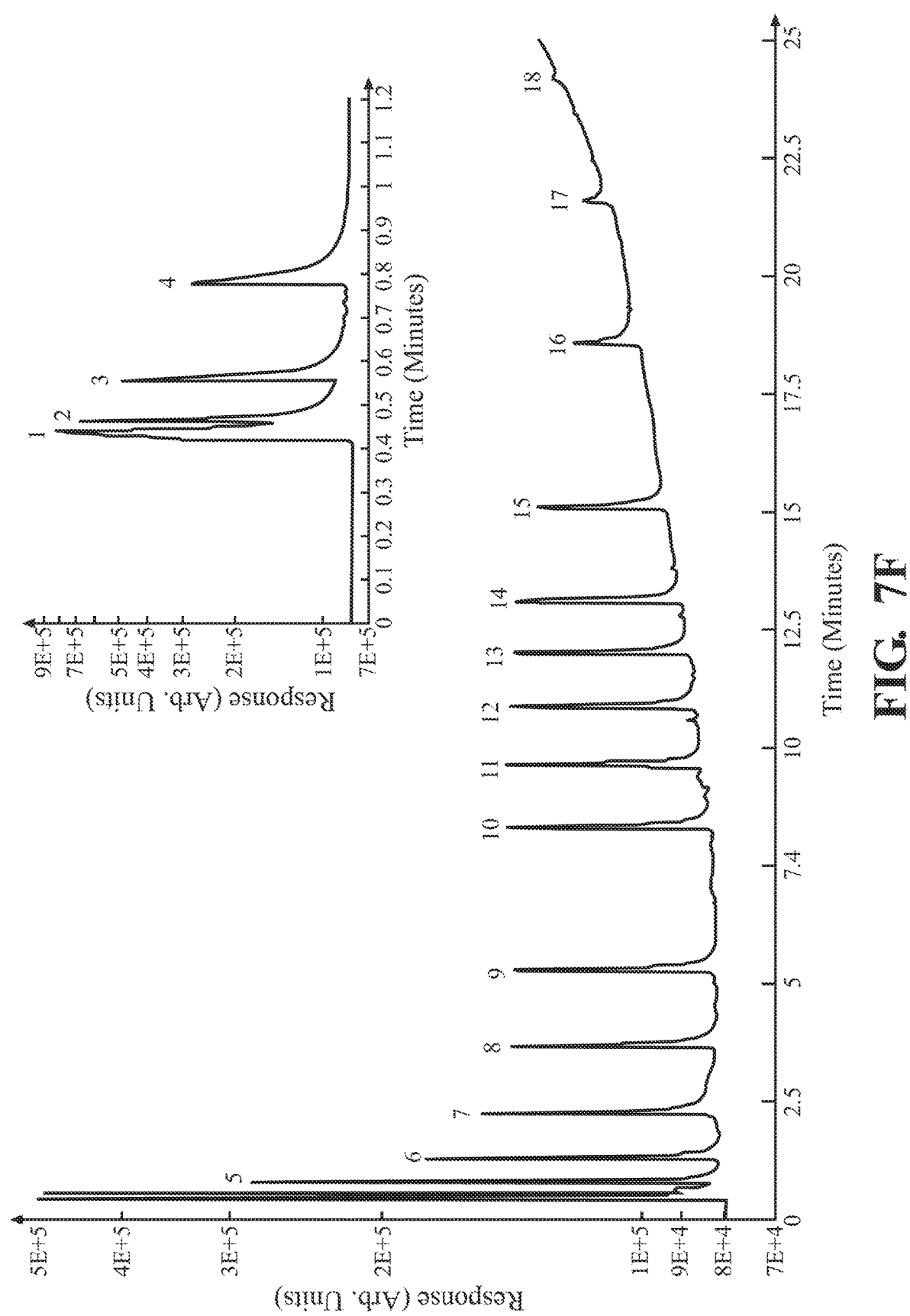
FIG. 7F is a graph showing a simulated distillation of ASTM 2887 in a μGC column showing the entire chromatogram with all the separated 18 components; the inset shows a zoom-in of the separation of the first four components.

We have successfully demonstrated a 2 m microfabricated gas chromatography (μGC) column comprised of a double Archimedean spiral design with a square cross-section of 100 μm×100 μm using silicon microfabrication techniques [26]. FIG. 7D is a SEM image of the μGC column showing the Archimedean spiral. FIG. 7E is a cross-sectional image of the μGC column. The microfabricated column was benchmarked against a 2 meter 100 μm diameter commercial column and the performance between the two columns was evaluated in tests performed under identical conditions. A vespel/graphite ferrule based compression sealing technique may be used to achieve leak-proof fluidic interconnection between the inlet tubing and the microchannel. As shown in FIGS. 7A-7C, the assembly may include a top plate 702, a bottom plate 704, a column nut 710 for connecting to the silica tubing 712, and a ferrule 708 on the top of the μGC column 706. This sealing technique enabled separations at temperatures up to 350° C. on the μGC column. The first high-temperature separations in microfabricated gas chromatographic columns of simulated distillation (ASTM 2887) and polycyclic aromatic hydrocarbons (EPA 8310) in temperature programmed mode is reported [26]. We used ASTM 2887, which consists of an alkane mixture with boiling points ranging from (21.9-545° C.). A common use for simulated distillation is to determine the boiling points of crude oils. However, in this work the simulated distillation was used to display the columns ability to operate at temperatures up to 350° C., the reasonable maximum temperature for use with the thermally cross-linked PDMS/2% vinyl stationary phase. The simulated distillation was started at 45° C. and was ramped to 350° C. at a rate of 15° C./min. FIG. 7F shows the obtained chromatogram showing 18 resolved components in the simulated distillation. Inset shows a zoom-in of the separation of the first four components.

The demonstrated μGC column along with the high temperature fixture offered one more solution towards potentially realizing a portable μGC device for the detection of semi-volatile environmental pollutants and explosives without the thermal limitations reported to date with μGC columns using epoxy based interconnect technology. However, this device did not have an integrated sensor and was instead connected to the flame ionization detector (FID) on a commercial GC column for the measurements.

Figure 8A:
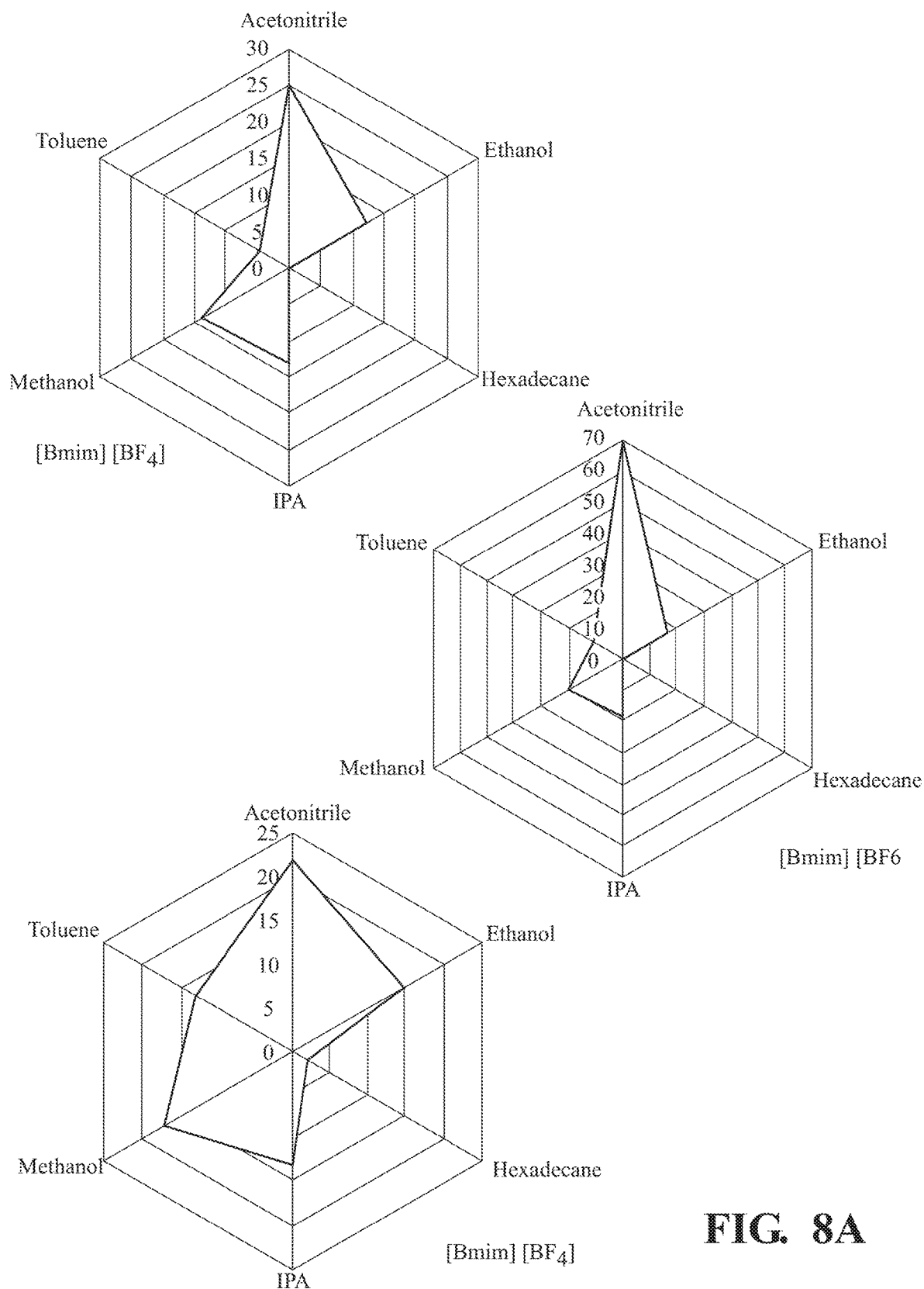
FIG. 8A are spider graphs showing typical sensitivity curves (in Hz/ppm) for six analytes on three different ILdIs consisting of 1:1 DPA-PS:BP:RTIL where the three RTILs are [Bmim][BF$_4$], [Bmim][PF$_6$], and [Bmpl][NTf$_2$]. For all the three ILdI's the frequency shift for toluene was positive whereas for all other analytes the slope is negative.
Figure 8B:
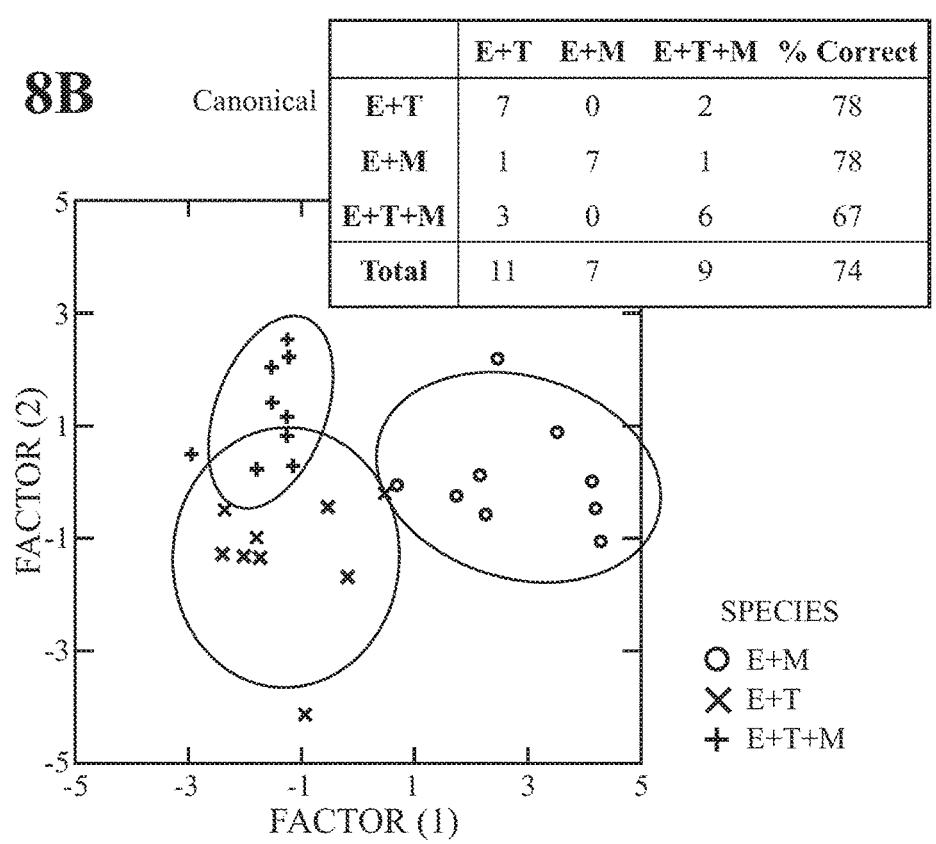
FIG. 8B is a discriminate analysis functional map of VOC mixtures analysed only with frequency shift.
Figure 8C:
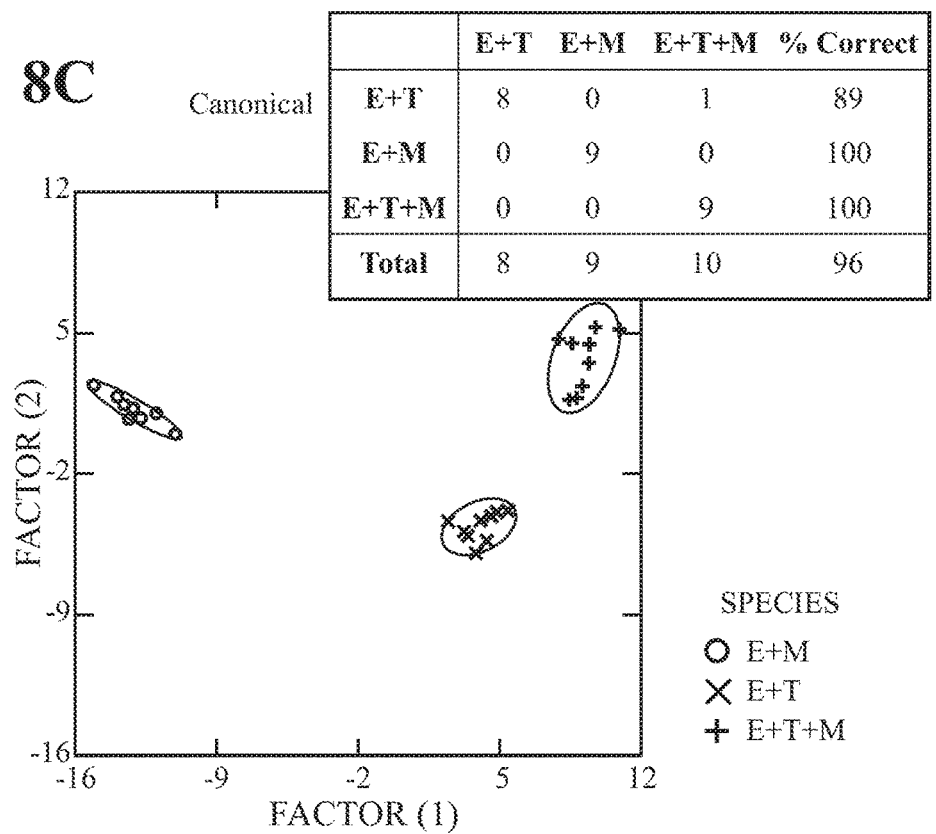
FIG. 8C is a discriminate analysis functional map of VOC mixtures analysed with both frequency and Q-factor changes.

Ionic Liquid Doped Ionomer (ILdI) Functionalized Resonator Arrays for Gas Mixture Discrimination In this work a new ionic liquid doped ionomer receptor layer was used to functionalize an array of monolithic, micromachined, quartz resonator gravimetric sensors for gas mixture discrimination applications [27, 28]. A recently developed polymer template, sulfonated poly(arylene ether sulfone)s with 1,3,5-s-triazin, abbreviated as DPA-PS:BP (1:1) was doped with five different room temperature ionic liquids to create a family of new receptor materials for volatile organic vapor detection and discrimination. The use of polymer template in the receptor coatings showed enhanced sensitivities to individual analytes and improved structural stability. DPA-PS:BP (1:1) polymer is capable of high RTIL intake capacity of up to 300 wt %, and can withstand operational temperatures of up to 400° C. Real-time, multiplexed measurement of mass loading ($\Delta f$) and the viscoelastic changes ($\Delta Q$) on four different ILdI functionalized pixels, upon analyte absorption/desorption, were made. FIG. 8A shows the response of three of the ILdI coated resonators to six volatile organic vapors and represented in a spider graph. It must be noted that for all the three ILdI's the frequency shift for toluene was positive (positive slope) whereas for all other analytes the slope is negative. However, in the spider graph the modulus of sensitivity is plotted for all cases. We used one parameter (f only) and two parameter ($\Delta f$, $\Delta Q$), based Linear Discriminant Analysis (LDA) to discriminate single, binary and ternary VOC analyte mixtures. Results showed that for single parameter LDA the best classification accuracy for binary and ternary mixtures was only 74%, as shown in FIG. 8B, whereas by using two parameter analysis we were able to obtain over 93% and 100% accuracy for ethanol/methanol and ethanol/toluene/methanol mixture respectively (FIG. 8C).

Calorimetric Sensing of Biochemical Reactions

The medical community is increasingly relying on affordable, miniature biosensors to evaluate and guide treatments.

Figure 9A:
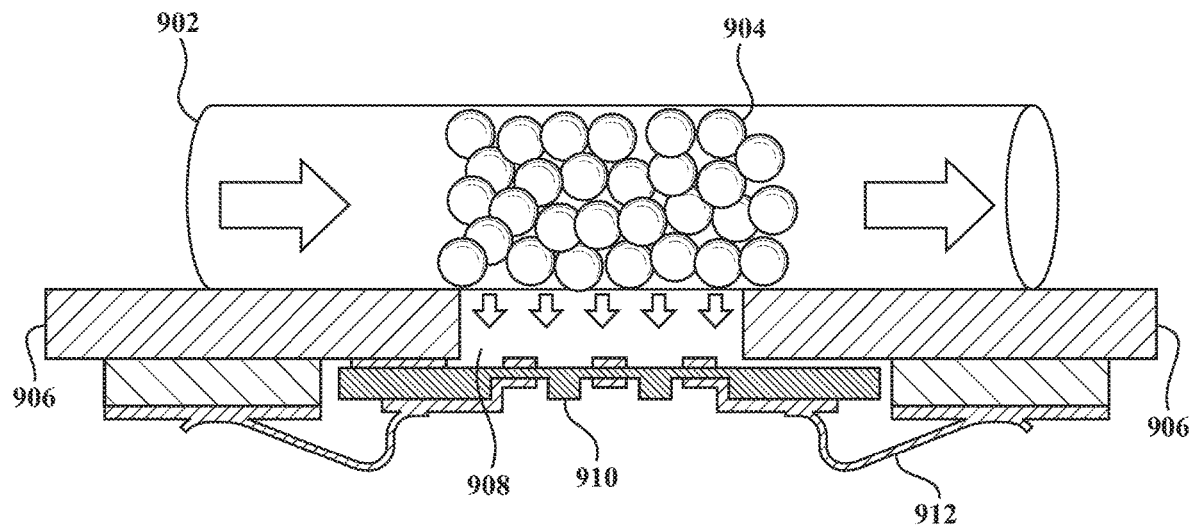
FIG. 9A is a cross-sectional schematic of a remotely coupled calorimetric biosensor based on a Y-cut temperature sensor.
Figure 9B:
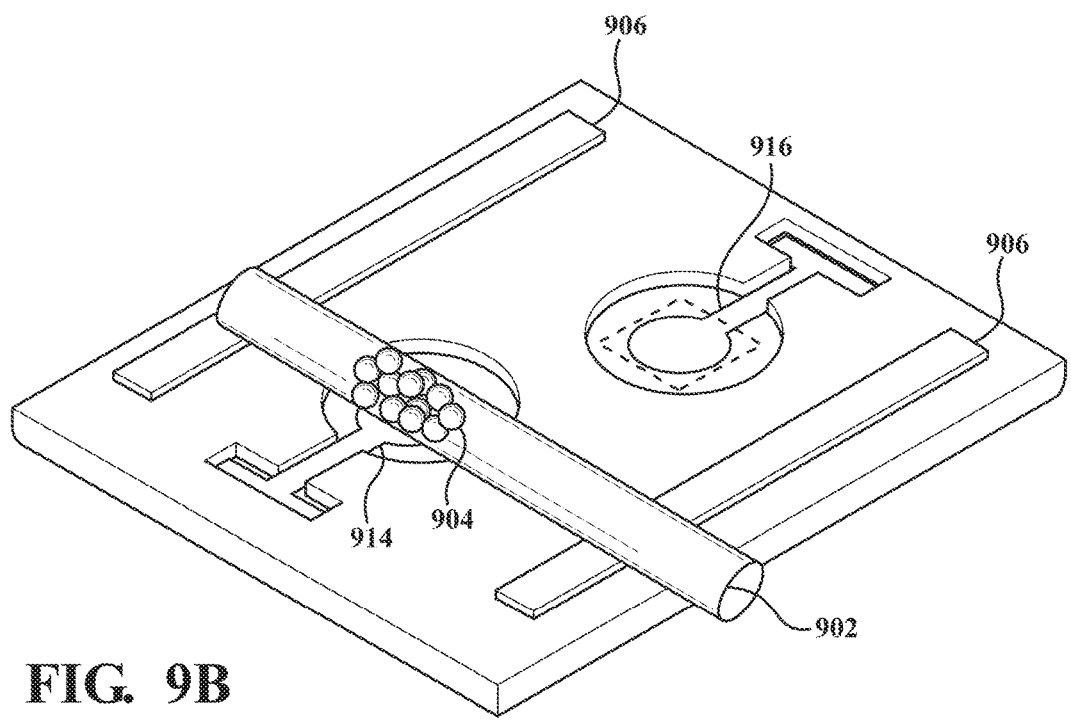
FIG. 9B is a schematic illustration of a differential measurement set-up.
Figure 9C:
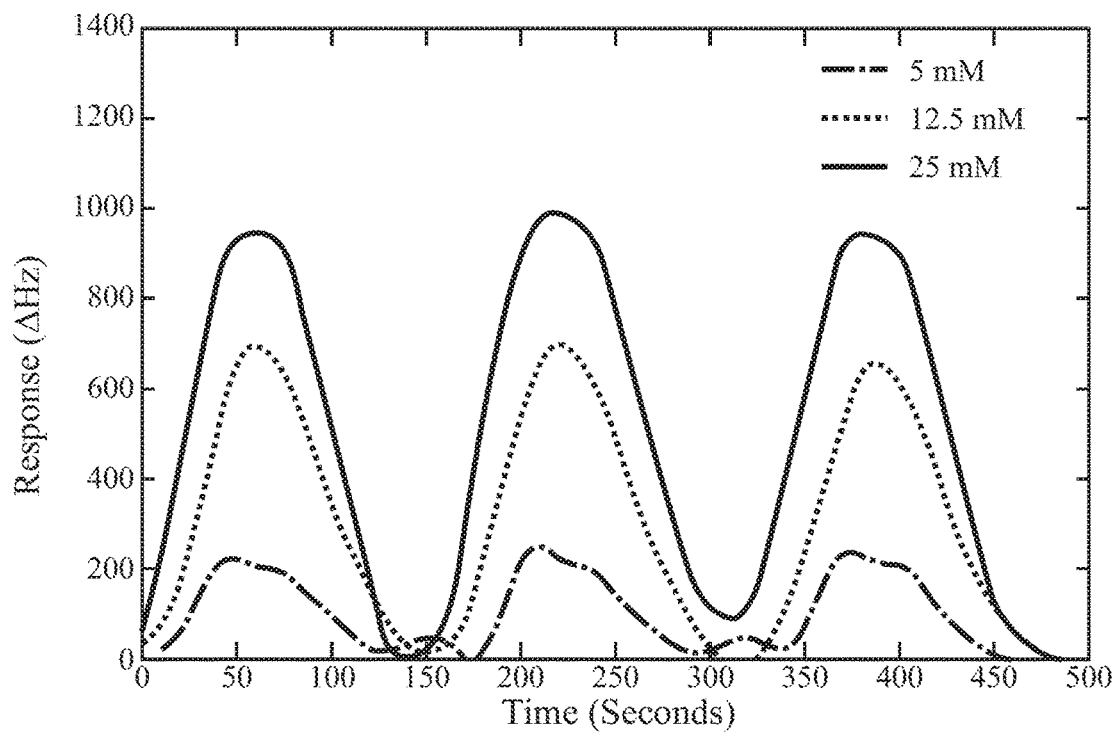
FIG. 9C is a graph of real-time enzymatically catalyzed signals upon creatinine flow through the immobilized enzyme.
Figure 9D:
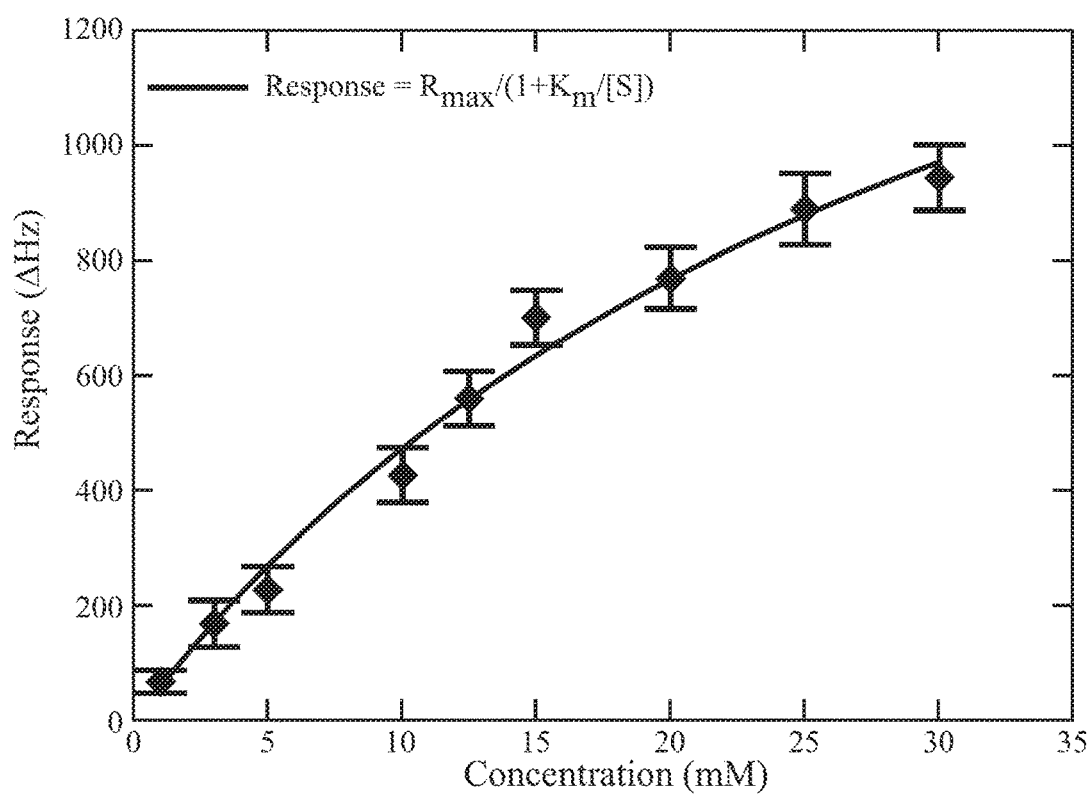
FIG. 9D is a graph of response of the system as a function of creatinine concentration.

These biosensors must be capable of analyzing small quantities of samples, have fast response times, and good operational stability. A particular bioanalyte of interest is creatinine. Both acute kidney injury and chronic kidney disease (CKD) rely on creatinine measurements for diagnoses. CKD has become a significant global health problem, with prevalence rates in the United States of 13% [29, 30]. CKD describes the gradual loss of kidney function ultimately resulting in end-state renal disease and dialysis treatment. Renal function is measured by quantifying creatinine, a well-established biochemical marker for renal function. We have recently demonstrated a calorimetric creatinine sensor based on ultrasensitive Y-cut, quartz bulk acoustic wave resonators as temperature sensors and remotely coupled the heat of reaction from enzyme mediated analyte reactions, as shown in FIGS. 9A and 9B. FIG. 9A is a cross-sectional schematic of a remotely coupled calorimetric biosensor based on a Y-cut temperature sensor. The Y-cut temperature sensor includes a glow tube 902 containing immobilized enzyme 904. The flow tube 902 is coupled to a resonator array 910 with a stainless steel spacer plate 906 in between and wire bonds 912 attached to the resonator array 910. Heat may be transferred from the flow tube to the resonator array through an air gap 908. FIG. 9B shows a perspective view of a differential measurement set-up, including a primary resonator 914 and a thermally isolated reference resonator 916. Y-cut quartz was chosen due to the very high-quality factors of the resonator that can be achieved and the phenomenological temperature sensitivity of +90 ppm/K [31] resulting in an exceptionally high temperature sensitivity of ~10 µK. The physical separation between the microfluidics and the temperature sensor allows for realizing disposable fluidic cartridges which can be custom designed for a variety of analytes on a single sensing platform [32]. By using layer by layer and alginate bead based enzyme immobilization techniques we have been able to achieve <1 mM urea and creatinine sensitivity mediated through urease and creatinine deiminase enzymes respectively. FIGS. 9C and 9D show real-time calorimetric response to creatinine flow and sensitivity respectively [33, 34]. However, the KAPTON® microfluidic flow channel used in this work has an inner diameter of 1.7 mm with a wall thickness of 30 µm. Therefore, for a 2 mm segment of the analyte interacting with the enzyme inside the tubing will end up heating a total analyte volume of 4.5 µl, consisting predominantly of water, before the signal is remotely coupled to the quartz temperature sensor. As compared to this, the volume of a spherical shell of diameter 750 µm is ~20 times smaller and will respond with a 20 times faster time constant. Furthermore, since the analyte is in direct contact with the spherical shell, the heat will be directly conducted to the shell through water and will result in a much larger temperature signal than when remotely coupled (through air). The thermal conductivity of water is ~23 times larger than that of air at atmospheric pressure and room temperature. Given the extraordinary temperature sensitivity of the WGM sensors of ≤50 µK this would easily allow for <10 µM sensitivity resolution for creatinine, the relevant range of creatinine in blood serum samples ranges from 50 µM-110 µM for normal function and >1 mM for CKD patients.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

REFERENCES

1. Carey, W. P., et al., *Selection of Adsorbates for Chemical Sensor Arrays by Pattern-Recognition*. Analytical Chemistry, 1986. 58(1): p. 149-153.
2. Rosepehrsson, S. L., et al., *Detection of Hazardous Vapors Including Mixtures Using Pattern-Recognition Analysis of Responses from Surface Acoustic-Wave Devices*. Analytical Chemistry, 1988. 60(24): p. 2801-2811.
3. Grate, J. W. and M. H. Abraham, *Solubility interactions and the design of chemically selective sorbent coatings for chemical sensors and arrays*. Sensors and Actuators B: Chemical, 1991. 3(2): p. 85-111.
4. Harsányi, G. b., *Polymer films in sensor applications: technology, materials, devices and their characteristics*. 1995, Lancaster, Pa.: Technomic Pub. Co. xxvi, 435 p.
5. Hierlemann, A., et al., *Polymer-Based Sensor Arrays and Multicomponent Analysis for the Detection of Hazardous Organic Vapors in the Environment*. Sensors and Actuators B-Chemical, 1995. 26(1-3): p. 126-134.
6. Nakata, S., et al., *Gas sensing based on a nonlinear response: Discrimination between hydrocarbons and quantification of individual components in a gas mixture*. Analytical Chemistry, 1996. 68(13): p. 2067-2072.
7. Heilig, A., et al., *Gas identification by modulating temperatures of SnO2-based thick film sensors*. Sensors and Actuators B-Chemical, 1997. 43(1-3): p. 45-51.
8. Tomchenko, A. A., et al., *Semiconducting metal oxide sensor array for the selective detection of combustion gases*. Sensors and Actuators B-Chemical, 2003. 93(1-3): p. 126-134.
9. Xie, C. S., et al., *Fabrication and formaldehyde gas-sensing property of ZnO-MnO2 coplanar gas sensor arrays*. Sensors and Actuators B-Chemical, 2010. 145(1): p. 457-463.
10. Lin, S. W., et al., *A selective room temperature formaldehyde gas sensor using TiO(2) nanotube arrays*. Sensors and Actuators B-Chemical, 2011. 156(2): p. 505-509.
11. van Herwaarden, A. W., et al., *Integrated thermopile sensors*. Sensors and Actuators A: Physical, 1989. 22(1-3): p. 621-630.
12. van Herwaarden, A. W., et al., *Liquid and gas microcalorimeters for (bio)chemical measurements*. Sensors and Actuators A: Physical, 1994. 43(1-3): p. 24-30.
13. Lerchner, J., D. Caspary, and G. Wolf, *Calorimetric detection of volatile organic compounds*. Sensors and Actuators B, 2000. 70: p. 57-66.
14. Zhang, Y. and S. Tadigadapa, *Calorimetric biosensors with integrated microfluidic channels*. Biosensors and Bioelectronics, 2004. 19(12): p. 1733.
15. Danielsson, B., *Calorimetric Biosensors*. J. Biotechnology, 1990. 15: p. 187-200.
16. Lee, W., et al., *High-sensitivity microfluidic calorimeters for biological and chemical applications*. Proceedings of the National Academy of Sciences, 2009. 106(36): p. 15225-15230.
17. Terry, S. C., J. H. Jerman, and J. B. Angell, *A gas chromatographic air analyzer fabricated on a silicon wafer*. Electron Devices, IEEE Transactions on, 1979. 26(12): p. 1880-1886.

18. Lambertus, G., et al., *Design, Fabrication, and Evaluation of Microfabricated Columns for Gas Chromatography*. Analytical Chemistry, 2004. 76(9): p. 2629-2637.
19. Agilent-Technologies. *5975T LTM Column Module* 2014.
20. Agah, M., et al., *High-performance temperature-programmed microfabricated gas chromatography columns*. Microelectromechanical Systems, Journal of, 2005. 14(5): p. 1039-1050.
21. Reidy, S., et al., *Temperature-Programmed GC Using Silicon Microfabricated Columns with Integrated Heaters and Temperature Sensors*. Analytical Chemistry, 2007. 79(7): p. 2911-2917.
22. Eklund, E. J. and A. M. Shkel, *Glass blowing on a wafer level*. Microelectromechanical Systems, Journal of, 2007. 16(2): p. 232-239.
23. Cho, J. Y., et al., *Fused-Silica Micro Birdbath Resonator Gyroscope*. Journal of Microelectromechanical Systems, 2014. 23(1): p. 66-77.
24. Gokhan, H., et al., *A highly aromatic and sulfonated ionomer for high elastic modulus ionic polymer membrane micro-actuators*. Smart Materials and Structures, 2012. 21(5): p. 055015.
25. Jin, X., L. Yu, and X. Zeng, *Enhancing the sensitivity of ionic liquid sensors for methane detection with polyaniline template*. Sensors and Actuators B: Chemical, 2008. 133(2): p. 526-532.
26. Gaddes, D., et al., *Improved micromachined column design and fluidic interconnects for programmed high-temperature gas chromatography separations*. Journal of Chromatography A, 2014. 1349: p. 96-104.
27. Min, H., G. Hatipoglu, and S. Tadigadapa. *Designing chemically selective microsensor arrays using ionic liquid doped ionomers*. in SENSORS, 2013 IEEE. 2013.
28. Min, H., G. Hatipoglu, and S. Tadigadapa, *Ionic Liquid doped Ionomer (ILdI) Functionalized Resonator Arrays for Gas Mixture Discrimination*. Analyst, 2016.
29. Vig, J. R., R. L. Filler, and Y. Kim, *Uncooled IR imaging array based on quartz microresonators*. Journal of Microelectromechanical Systems, 1996. 5(2): p. 131-137.
30. Ren, K., et al., *Monitoring biochemical reactions using Y-cut quartz thermal sensors*. Analyst, 2011. 136: p. 2904-2911.
31. Gaddes, D. and S. Tadigadapa, *A calorimetric Biosensing System for Quantification of Urinary Creatinine*. ACS Sensors, 2 (6), pp 796-802, 2017.
32. Gaddes, D. E., et al., *Remote calorimetric detection of urea via flow injection analysis*. Analyst, 2015. 140(23): p. 8033-8040.
33. Cross, G. H., Y. Ren, and M. J. Swann, *Refractometric discrimination of void-space filling and swelling during vapour sorption in polymer films*. Analyst, 2000. 125(12): p. 2173-2175.
34. Ksendzov, A., M. L. Homer, and A. M. Manfreda, *Integrated optics ring-resonator chemical sensor with polymer transduction layer*. Electronics Letters, 2004. 40(1): p. 63-65.
35. Podgorsek, R. P. and H. Franke, *Selective optical detection of aromatic vapors*. Applied Optics, 2002. 41(4): p. 601-608.
36. Sun, Y. and X. Fan, *Analysis of ring resonators for chemical vapor sensor development*. Optics Express, 2008. 16(14): p. 10254-10268.
37. Shopova, S. I., et al., *On-Column Micro Gas Chromatography Detection with Capillary-Based Optical Ring Resonators*. Analytical Chemistry, 2008. 80(6): p. 2232-2238.
38. Potyrailo, R. A. and T. M. Sivavec, *Boosting Sensitivity of Organic Vapor Detection with Silicone Block Polyimide Polymers*. Analytical Chemistry, 2004. 76(23): p. 7023-7027.
39. Qiulin, M., R. Tobias, and G. Zhixiong, *Temperature sensitivity of silica micro-resonators*. Journal of Physics D: Applied Physics, 2008. 41(24): p. 245111.
40. Chenchen, Z., G. Hatipoglu, and S. Tadigadapa, *High-Speed Ultrasmooth Etching of Fused Silica Substrates in $SF_6$, $NF_3$, and $H_2O$-Based Inductively Coupled Plasma Process*. Microelectromechanical Systems, Journal of, 2015. 24(4): p. 922-930.
41. Tigelaar, D. M., et al., *Synthesis and Properties of Novel Proton-Conducting Aromatic Poly(ether sulfone)s That Contain Triazine Groups*. Macromolecules, 2009. 42(6): p. 1888-1896.
42. Jin, X., et al., *Ionic Liquid High-Temperature Gas Sensor Array*. Analytical Chemistry, 2006. 78(19): p. 6980-6989.
43. Moerman, I., P. P. V. Daele, and P. M. Demeester, *A review on fabrication technologies for the monolithic integration of tapers with III-V semiconductor devices*. IEEE Journal of Selected Topics in Quantum Electronics, 1997. 3(6): p. 1308-1320.
44. Michels, T. and V. Aksyuk, *Cavity optical transducer platform with integrated actuation for multiple sensing applications*, in Solid State Sensors, Actuators, and Microsystems Workshop 2016, Transducers Research Foundation: Hilton Head Island, S.C. p. 4.
45. Almeida, V. R., R. R. Panepucci, and M. Lipson, *Nanotaper for compact mode conversion*. Optics Letters, 2003. 28(15): p. 1302-1304.
46. Gaddes, D. and S. Tadigadapa, *A calorimetric Biosensing System for Quantification of Urinary Creatinine*. ACS Sensors, 2017. To be Submitted for Publication in 2018.
47. Kao, P., D. Allara, and S. Tadigadapa, *Study of Adsorption of Globular Proteins on Hydrophobic Surfaces*. Sensors Journal, IEEE, 2011. 11(11): p. 2723-2731.
48. Pisani, M. B., Ren, K., Kao, P., and Tadigadapa, S., *Application of micromachined Y-cut quartz bulk acoustic wave resonator for infrared sensing*. Journal of Microelectromechanical Systems, 2011. 20(1): p. 288-296.
49. Kao, P., et al., *Volumetric interpretation of protein adsorption: Interfacial packing of protein adsorbed to hydrophobic surfaces from surface-saturating solution concentrations*. Biomaterials, 2011. 32(4): p. 969-978.

The invention claimed is:

1. A sensing and analysis system on a chip for sensing and analyzing chemical or biological analytes, comprising:
   a chromatography column having an inlet and an outlet comprised within the chip for temporal separation of components of analytes, the chromatography column having a first wafer layer forming the chromatography column; and
   two whispering gallery mode (WGM) optical resonators for sensing of the components of the analytes, the first WGM optical resonator having a hollow sealed enclosure located over the inlet and the second WGM optical resonator having a hollow sealed enclosure located over the outlet of the chromatography column, wherein a gas flowing through the chromatography column fills the hollow sealed enclosures, and each WGM optical resonator further having an optical waveguide aligned with the sealed hollow enclosure.

2. The sensing and analysis system on a chip according to claim 1, wherein the chromatography column has a double Archimedean spiral geometry.

3. The sensing and analysis system on a chip according to claim 1, wherein the hollow sealed enclosure is the shape of a spherical shell, a toroidal shell, or a double-walled shell.

4. The sensing and analysis system on a chip according to claim 1, wherein the hollow sealed enclosure is a shell of any thickness and shape blown out using a planar glass blowing technique.

5. The sensing and analysis system on a chip according to claim 1, wherein the hollow sealed enclosure is comprised within a glass layer, wherein the glass layer is etched, aligned and bonded to the first wafer layer.

6. The sensing and analysis system on a chip according to claim 1, wherein the hollow sealed enclosure is a spherical shell having a diameter ranging from 50 μm to 1 mm.

7. The sensing and analysis system on a chip according to claim 1, wherein a channel of the chromatography column has a cross-section having a dimension ranging from 100 micron×100 micron to 500 micron×500 micron.

8. The sensing and analysis system on a chip according to claim 1, wherein the chromatography column has a length ranging from 1 m to 10 m.

9. The sensing and analysis system on a chip according to claim 1, wherein the hollow sealed enclosure is in the path of a gas flow of the analytes.

10. The sensing and analysis system on a chip according to claim 1, wherein the hollow sealed enclosure is out of the path of a gas flow of the analytes.

11. The sensing and analysis system on a chip according to claim 5, further comprising a third wafer layer having the optical waveguides attached thereon and through holes etched therein so as to allow for the hollow sealed enclosure to be able to pass therethrough, wherein the third wafer layer is aligned and bonded to the glass layer, and further wherein a top surface of the third wafer layer is at an equatorial plane of the hollow sealed enclosure, the three wafer layers are stacked and bonded together and the optical waveguide is positioned to achieve optimal coupling of an evanescent wave into the hollow enclosure.

12. The sensing and analysis system on a chip according to claim 1, wherein the optical waveguide tapers towards the hollow sealed enclosure for achieving optimal coupling of the evanescent wave into hollow sealed enclosure.

13. The sensing and analysis system on a chip according to claim 1, wherein the chromatography column and the inner surface of the hollow sealed enclosure each comprise a room temperature ionic liquid (RTIL) in a polymeric matrix.

14. The sensing and analysis system on a chip according to claim 13, wherein the chromatography column and the inner surface of the hollow sealed enclosure each comprise polydimethylsiloxane (PDMS).

15. A calorimetric sensing system on a chip, comprising:
   a first wafer layer molded to form an inlet chamber, a micro-fluidic channel and a reactor chamber;
   at least one whispering gallery mode (WGM) optical resonator having a hollow sealed enclosure formed over and integrated with the reactor chamber, the at least one WGM optical resonator further having an optical waveguide aligned with the hollow sealed enclosure for calorimetric coupling; and
   wherein when a selective biocatalyst of interest is placed in the microfluidic channel, the heat generated or absorbed upon reaction of a bioanalyte of interest with the biocatalyst is coupled to the WGM optical resonator, whereby the bioanalyte of interest is detected.

16. The calorimetric sensing system on a chip according to claim 15, wherein the microchannel is made of PDMS, any soft polymer, 3-D printed plastic, silicon, ceramic, or a biocompatible material.

17. The calorimetric sensing system on a chip according to claim 15, wherein the hollow sealed enclosure in the calorimetric sensing system is constructed of any glass composition capable of softening in the temperature range of 0-2000° C.

18. The calorimetric sensing system on a chip according to claim 15, wherein the selective biocatalyst of interest is any selective molecules, enzymes, or proteins, or cells or a mixture thereof.

* * * * *